(12) United States Patent
Desu-Kalyanam

(10) Patent No.: US 11,197,602 B2
(45) Date of Patent: Dec. 14, 2021

(54) CLEANING AND DISINFECTING ITEMS

(71) Applicant: AISHWARYA, LLC, Scottsdale, AZ (US)

(72) Inventor: Anu R. Desu-Kalyanam, Phoenix, AZ (US)

(*) Notice: Subject to any disclaimer, the term of this patent is extended or adjusted under 35 U.S.C. 154(b) by 0 days.

(21) Appl. No.: 16/882,814

(22) Filed: May 26, 2020

(65) Prior Publication Data

US 2020/0281444 A1 Sep. 10, 2020

Related U.S. Application Data

(62) Division of application No. 15/844,631, filed on Dec. 18, 2017, now Pat. No. 10,702,126.

(51) Int. Cl.

| | |
|---|---|
| A47L 23/00 | (2006.01) |
| A47L 23/26 | (2006.01) |
| A47L 23/20 | (2006.01) |
| A46B 15/00 | (2006.01) |
| A46B 13/02 | (2006.01) |
| A61L 2/10 | (2006.01) |
| B08B 1/00 | (2006.01) |
| B08B 7/00 | (2006.01) |
| G01N 21/47 | (2006.01) |
| G01N 21/33 | (2006.01) |
| A61L 2/24 | (2006.01) |

(52) U.S. Cl.
CPC ......... *A47L 23/263* (2013.01); *A46B 13/023* (2013.01); *A46B 15/0034* (2013.01); *A47L 23/205* (2013.01); *A61L 2/10* (2013.01); *A61L 2/24* (2013.01); *B08B 1/002* (2013.01); *B08B 1/008* (2013.01); *B08B 7/0057* (2013.01); *G01N 21/33* (2013.01); *G01N 21/474* (2013.01); *A46B 2200/306* (2013.01); *A47L 2601/10* (2013.01); *A61L 2202/14* (2013.01)

(58) Field of Classification Search
CPC ... A47L 23/00; A47L 23/02; A46B 2200/306; A46B 15/0034
See application file for complete search history.

(56) References Cited

U.S. PATENT DOCUMENTS

| | | | | |
|---|---|---|---|---|
| 2,768,404 A | * | 10/1956 | Frank | A47L 23/16 |
| | | | | 15/258 |
| 9,661,983 B1 | * | 5/2017 | Gonzales | A47L 23/26 |

* cited by examiner

*Primary Examiner* — Michael D Jennings

(57) ABSTRACT

Devices, systems and methods for cleaning and disinfecting footwear items are disclosed herein. In an aspect, an apparatus is disclosed comprising an ultraviolet light element configured to emit ultraviolet light toward a top covering element configured to receive one or more contaminated item, wherein the ultraviolet light element is located within a lower frame element. In another aspect, a grating element is disclosed comprising a frame of bars configured to support the one or more contaminated item; wherein the grating element is a ceiling enclosure portion of the lower frame element. In yet another aspect, a brush frame element mounted to an underside of the grating element is disclosed, wherein the brush frame element comprises a set of brush strips configured to protrude through at least one space between the frame bars.

10 Claims, 26 Drawing Sheets

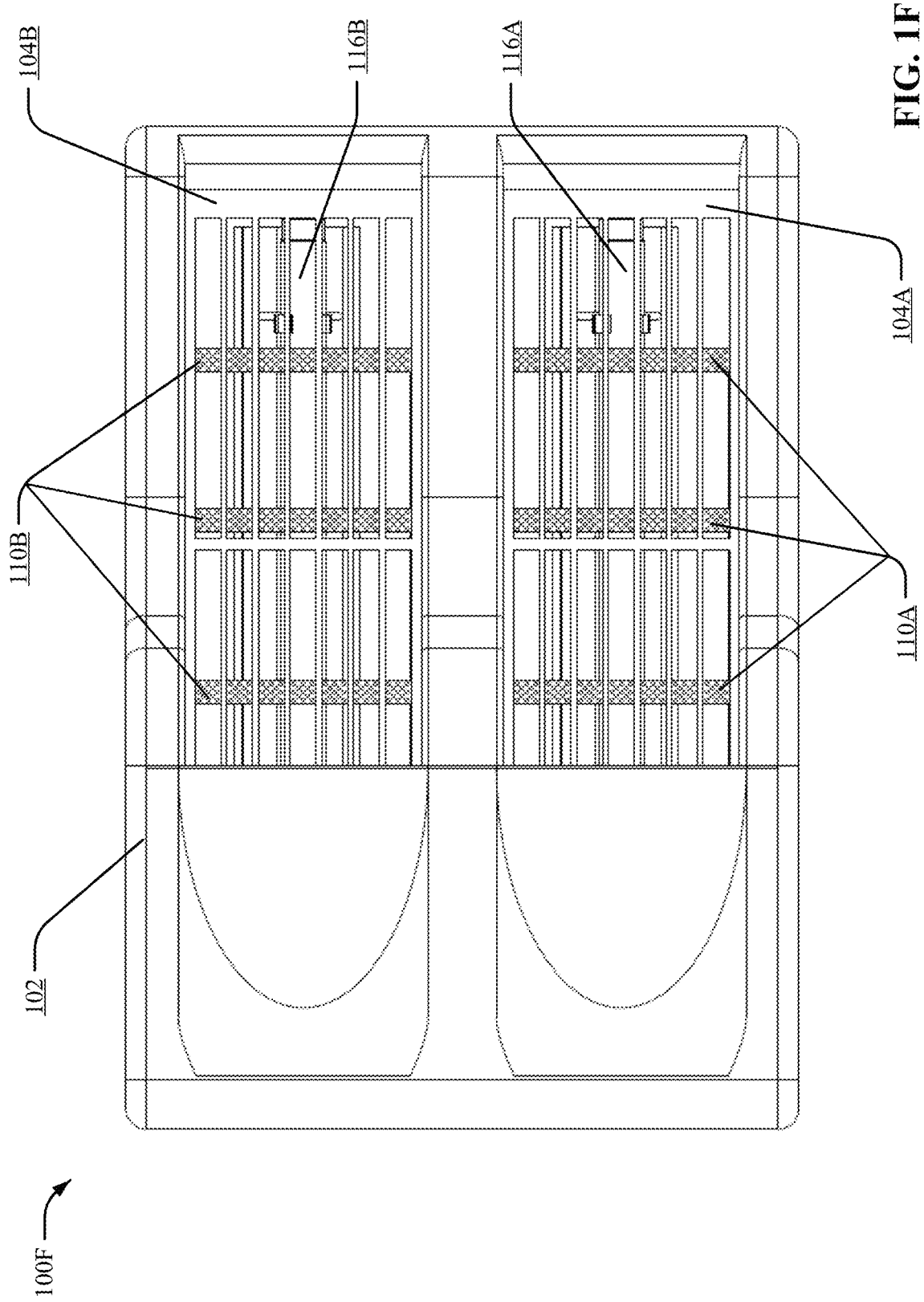

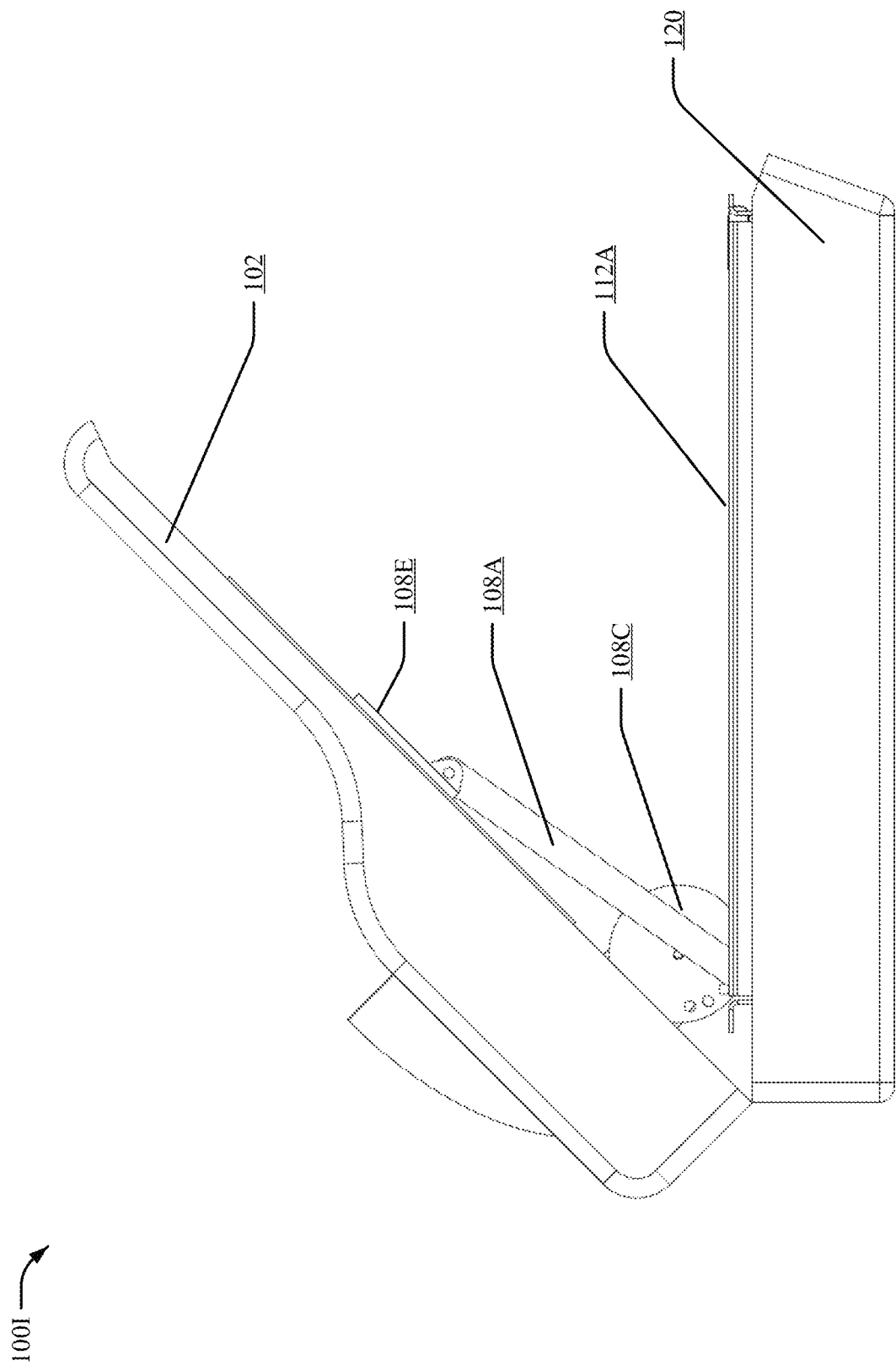

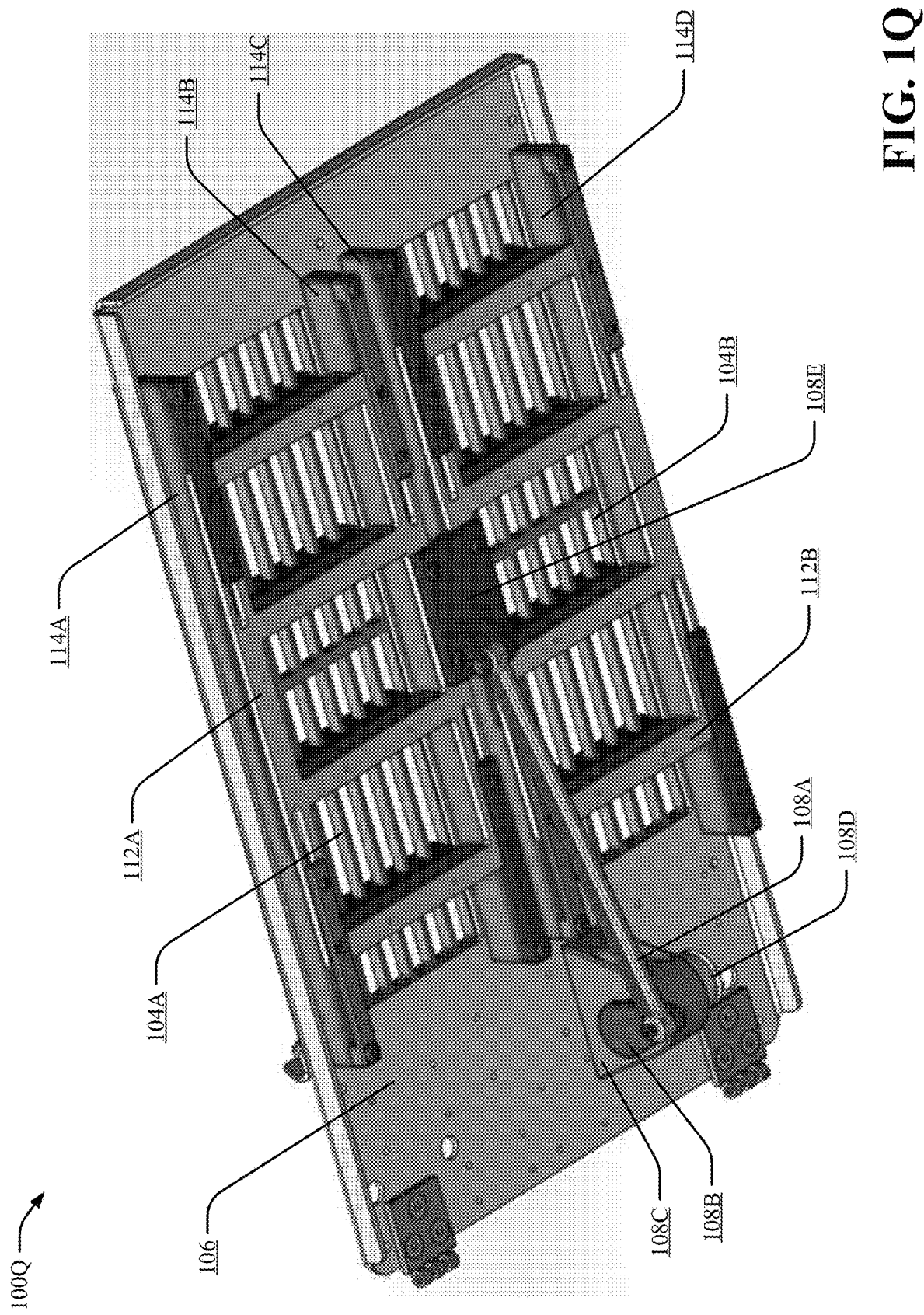

CLEANING AND DISINFECTING ITEMS

CROSS REFERENCED TO RELATED APPLICATION

This divisional patent application claims the benefit of U.S. patent application Ser. No. 15/844,631 entitled "CLEANING AND DISINFECTING ITEMS" and filed on Dec. 18, 2017, the entirety of which application is hereby incorporated by reference herein.

TECHNICAL FIELD

This disclosure relates to systems, devices and methods for cleaning and disinfecting footwear.

BACKGROUND

Traditionally, before entering an indoor establishment, such as a home, office or building, an entrant wipes his or her shoes (e.g. using a doormat, welcome mat, carpet, etc.). While the act of wiping shoes superficially removes some debris from the sole of the shoe, there still remain germs, debris, micro-organisms, bacteria, dirt, dust, and other such unsanitary matter. In an instance, a sample of shoes were found to have nine different species of bacteria including bacteria capable of causing stomach, eye, and lung infection. Often, coliform, a bacteria mostly derived from human and animal waste, can be found on footwear. Furthermore, in one research study, footwear was observed to transfer bacteria to tile floors in a household ninety percent of the time. Carpets are also known to harbor significant amounts of bacteria brought in from external sources. As compared to a toilet seat, which can be found to house thousands of bacteria, footwear can harbor millions of bacteria. The amount of unsanitary matter present on a persons shoes is generally understood.

Given the unsanitary nature of people's footwear, there exists a risk of transferrence of infection, bacteria, and viruses to indoor environments and the people who occupy such environemnts. For instance, children who often spend time on the floor playing are vulnerable to germs tracked into a home, especially provided some children are prone to placing hands in their mouth or using hands to rub their eyes. Generally, unsanitary material is easily tracked into homes, offices and other spaces as a result of insufficient cleaning and disinfecting of footwear prior to entering a space. Currently, the existing mechasnisms for cleaning footwear are insufficient at disinfecting the footwear. There is a significant need for devices or tools to better disinfect, clean, and remove unsanitary matter from a persons footwear in an efficient and convenient manner.

SUMMARY

The following presents a simplified summary of the disclosure in order to provide a basic understanding of some aspects of the disclosure. This summary is not an extensive overview of the disclosure. It is intended to neither identify key or critical elements of the disclosure nor delineate any scope particular embodiments of the disclosure, or any scope of the claims. Its sole purpose is to present some concepts of the disclosure in a simplified form as a prelude to the more detailed description that is presented later.

In accordance with one or more embodiments and corresponding disclosure, various non-limiting aspects are described in connection with disinfecting and cleaning footwear. In accordance with a non-limiting embodiment, in an aspect, an apparatus is provided comprising an ultraviolet light element configured to emit ultraviolet light toward a top covering element configured to receive one or more contaminated item, wherein the ultraviolet light element is located within a lower frame element. In another aspect, the apparatus comprises a frame of bars configured to support the one or more contaminated item; wherein the grating element is a ceiling enclosure portion of the lower frame element. In yet another aspect, the apparatus comprises a brush frame element mounted to an underside of the grating element, wherein the brush frame element comprises a set of brush strips configured to protrude through at least one space between the frame bars. In another non-limiting embodiment, the apparatus can further comprise a reciprocating drive assembly connected to the second brush guide and the third brush guide, wherein the reciprocating drive element is configured to generate a rotational motion capable of moving the set of brush strips against the one or more contaminated item.

The disclosure further discloses a method, comprising receiving, by a system comprising a processor, a set of sensor data, wherein the set of sensor data represents force information related to a grating element of the system. In another aspect, the method can include activating, by the system, a reciprocation drive assembly of the system that moves a set of brush strips in contact with a contaminated item based on a receipt of the set of sensor data. In yet another aspect, the method can further include emitting, by the system, ultraviolet light from an ultraviolet light element based on a receipt of the set of sensor data.

The following description and the annexed drawings set forth certain illustrative aspects of the disclosure. These aspects are indicative, however, of but a few of the various ways in which the principles of the disclosure may be employed. Other advantages and novel features of the disclosure will become apparent from the following detailed description of the disclosure when considered in conjunction with the drawings.

BRIEF DESCRIPTION OF THE DRAWINGS

FIG. 1F illustrates a top viewpoint providing a perspective view from an aerial vantage point of an example non-limiting system for disinfecting a contaminated item in accordance with one or more implementation described herein.

FIG. 1I illustrates a side view point of an example non-limiting system for disinfecting a contaminated item in an open position in accordance with one or more implementation described herein.

FIG. 1Q illustrates an example non-limiting view of an underside of a top plate element of a system for disinfecting a contaminated item in accordance with one or more implementation described herein.

FIG. 9 is a schematic block diagram of a sample-computing environment in accordance with various aspects and embodiments.

DETAILED DESCRIPTION

Overview

The following detailed description is merely illustrative and is not intended to limit embodiments and/or application or uses of embodiments. Furthermore, there is no intention to be bound by any expressed or implied information presented in the preceding Background or Summary sections, or in the Detailed Description section. One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

By way of introduction, the subject matter disclosed in this disclosure relates to an automated device for cleaning footwear of all varieties such as sandals, high heels, tennis shoes, dress shoes, and other such footwear items. In some embodiments, the device is designed to facilitate disinfection, removal of debris, and general cleaning of a user's footwear in an easy to use, automated, and/or quick manner. In some embodiments, the cleaning and disinfecting can include the removal of undesired larger sized contaminants such as dust, dirt, debris, and other larger objects present on the bottom surface of the footwear item. In other embodiments, the cleaning and disinfecting can also include the disinfecting of smaller sized contaminants such as bacteria, particles, and other smaller contaminants via ultraviolet light emissions.

It should be appreciated that various embodiments herein may utlize a variety of mechanical technologies (e.g. motors, processors, power source, sensors, etc.) having different properties. Accordingly, an automated device for cleaning and disinfecting footwear as well as the elements that comprise such device are described herein. Some or all of the above needs may be addressed by certain embodiments of the invention. Implementations may include one or a combination of any two or more of the aforementioned features. These and other aspects, features, implementations, and advantages, and combinations of them, can be expressed as methods, apparatus, systems, components, program products, business methods, and means or steps for performing functions, or combinations of them. Other features, aspects, implementations, and advantages will become apparent from the description, the drawings, and the claims.

Example Device for Cleaning and Disinfecting Footwear

Figure 1A:
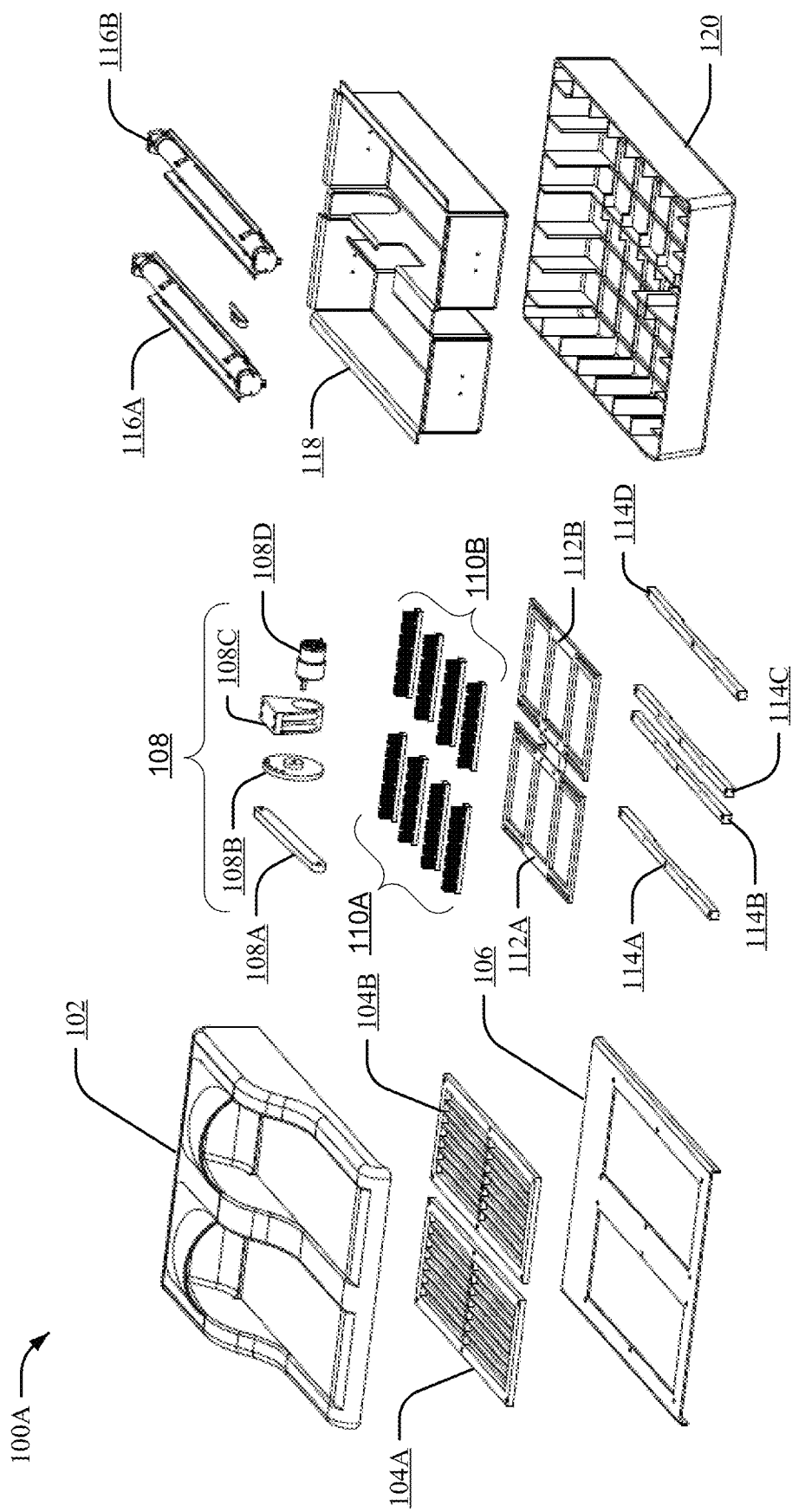
FIG. 1A illustrates an exploded view of an example non-limiting system for disinfecting a contaminated item in accordance with one or more implementation described herein.

Referring now to the drawings, FIG. 1A illustrates an exploded view of an example non-limiting system 100A for disinfecting a contaminated item in accordance with one or more implementation described herein. In an aspect, systems can be employed as devices comprising processors as well.

In an aspect, system 100A can comprise one or more components including, but not limited to, top covering 102, first grating element 104A, second grating element 104B, top plate element 106, first brush strips 110A, second brush strips 110B, first brush frame 112A, second brush frame 112B, first brush guide 114A, second brush guide 114B, third brush guide 114C, fourth brush guide 114D, first light assembly 116A, second light assembly 116B, lower frame 118, bottom cover 120, and reciprocating drive 108 comprising connecting rod 108A, motor mount 108B, cam lever 108C, and gear motor 108D. In an aspect, one or more of the components and/or elements of system 100A can be electrically and/or communicatively coupled to one or more devices of system 100A or other embodiments to perform one or more functions described herein.

In an aspect, system 100A can disinfect and/or clean a contaminated footwear item or other contaminated item by employing one or more of its system components and/or elements. In an aspect, system 100A can employ one or more ultraviolet light element (e.g., first light assembly 116A and/or second light assembly 116B) configured to emit ultraviolet light toward a top covering element 102 configured to receive one or more contaminated item, wherein the ultraviolet light element is located within a lower frame element 118. In another aspect, system 100A can also comprise a grating element (e.g., first grating element 104A and/or second grating element 104B) comprising a frame of bars configured to support the one or more contaminated item; wherein the grating element is a ceiling enclosure portion of the lower frame element 118. In yet another aspect, system 100A can also employ a brush frame element (e.g., first brush frame element 112A and/or second brush frame element 112B) mounted to an underside of the grating element, wherein the brush frame element comprises a set of brush strips (e.g., first brush strips 110A, second brush strips 110B) configured to protrude through at least one space between the frame bars.

In an aspect, system 100A can include top covering element 102 which can function to provide a housing that encloses system 100A components from exposure to the outside environment. In another aspect, top covering element 102 can provide sufficient space to house electronics associated with system 100A. Furthermore, in an aspect, top covering element 102 can protect and shield a user from ultraviolet light emitted from first light assembly 116A and/or second light assembly 116B that may emanate beyond an underneath surface of a footwear item. For instance, a user may stand on a first grating element 104A with a left shoe and a second grating element with a right shoe and upon the emission of ultraviolet light towards the base of the shoe, some ultraviolet light may escape beyond the upper edges of the shoes and can contact an awning of top covering element 102 thus protecting a user (e.g., skin) from coming into contact with the ultraviolet light.

In a non-limiting embodiment, top covering element 102 can integrate with other elements of system 100A such as a reciprocating motor assembly (e.g., reciprocating drive 108), a brushing assembly (e.g., first brush guide 114A, second brush guide 114B), and/or a metal grating (e.g., first grating element 104A, second grating element 104B). In another aspect, top covering element 102 can be fabricated from any of several materials. For instance, in a non-limiting embodiment, top covering element 102 can be fabricated from a plastic material such as nylon for instance. In yet another aspect, top covering element 102 can connect to bottom covering element 120 via any interlinking mechanism such as a hinge (e.g., see system 100Q below). In an aspect, top covering element 102 can be opened at such hinge to expose internal elements and/or components of system 100A such that a user can access such components.

For instance, a user may need to change an ultraviolet light bulb and thus can open top covering element 102 to gain access to first light assembly 116A and/or second light assembly 116B. In another instance, a user may open top covering element 102 in order to access first grating element 104A and/or second grating element 104B to remove and clean such component part. In yet another instance, the top covering element 102 can be opened in order to access first brush strips 110A and/or second brush strips 110B to change out worn out brushes or clean such used brushes. In another aspect, the hinge can be configured to allow the top covering element 102 to pivot and/or open in any of several directions such as vertically, horizontally, and/or diagonally. In another non-limiting embodiment, system 100A can connect top covering element 102 to bottom covering element 120 with a snap-fit mechanism instead of a hinge mechanism. Furthermore, in other non-limiting embodiments the top covering element 102 can include no hinge but rather be removable as a lift-off cover. In another aspect, top covering element 102 can cover the elements of system 100A in multiple parts.

In an aspect, top covering element 102 can be comprised of any of a variety of materials including, but not limited to, thermoplastics, polyethylene, polystyrene, and other synthetic materials. Furthermore, in an aspect encasing resins can be applied to such materials as well. In yet another aspect, top covering element 102 can be configured into a variety of shapes. For instance, in a non-limiting embodiment, the awning portion of top covering element 102 can be configured to shield a user eyes from ultraviolet light emitted beyond the footwear item perimeter. In another non-limiting embodiment, the top covering element 102 can comprise an awning portion that is extended to cover more than the frontal portion of a shoe. Accordingly, the awning portion can be configured to cover the entire shoe area (e.g., around and above each foot) such that no ultraviolet light can escape beyond the shielded portion.

Furthermore, in an aspect, an opening (e.g., semicircular) in the awning can be cutout in order to allow an ankle or leg to be inserted within such opening. In another non-limiting embodiment, an awning covering the frontal portion of the shoe or an awning covering the entire footwear item and grating element can be lined with mirrors on the underside of such awnings in order to reflect escaped ultraviolet light emitted beyond the grating elements back onto the footwear item or back down towards system 100A. In yet another embodiment, mirrors can line the inner portion of lower frame 118 and/or bottom covering element 120 in order to reflect stray ultraviolet light towards locations on the lower surface of the footwear item.

In another aspect, system 100A can include a first grating element 104A and a second grating element 104B. In a non-limiting embodiment, first grating element 104A and a second grating element 104B are configured to allow a user wearing footwear to mount a surface (e.g., surface of first grating element 104A and second grating element 104B) of system 100A. As such, in a non-limiting embodiment, first grating element 104A and second grating element 104B can be configured to support individuals weighing 300 pounds or more in weight. Furthermore, first grating element 104A and second grating element 104B can be configured with regularly spaced parallel elongated elements such as rods, bars, and/or columns. Accordingly, in a non-limiting embodiment, the grating of first grating element 104A and second grating element 104B can take the form of meshing or a grid-like structure.

In any of several embodiments, the openings in first grating element 104A and second grating element 104B can leave openings of space between the grating structure such that brushes located below the grating elements can protrude through such spaces and contact the lower surface of the footwear item. In any of several embodiments, the spacing between the grates can be wider or narrower configurations to accommodate different sized (e.g., larger, smaller, finer, coarser, etc.) brushes protruding through the grates. Accordingly, first grating element 104A and second grating element 104B can provide a mounting surface for a first and second brushing assembly (e.g., which can vary in specifications).

In an aspect, as the brushes touch a lower surface of a footwear item (e.g., shoe, sandal, etc.), the brushes can move in various directions (e.g., laterally, circular, sweeping motion, etc.) to remove and/or bat away contaminants, filth, and debris from the lower surface of the footwear item. In an aspect, first grating element 104A and second grating element 104B can integrate with other system 100A elements and components, including, but not limited to, top covering element 102, reciprocating drive 108 (including connecting rod 108A, motor mount 108B, cam lever 108C, gear motor 108D, etc.), first brush frame 112A, second brush frame 112B, first brush guide 114A, second brush guide 114B, third brush guide 114C, and/or fourth brush guide 114D.

In an aspect, first grating element 104A and second grating element 104B can be fabricated with a water jet machining system. In another aspect, the grating elements can be comprised of a metallic material and in a non-limiting embodiment are capable of supporting over 300 pounds of weight. In a non-limiting embodiment, first grating element 104A and second grating element 104B can include a panel element capable of installation on or removal from a top surface of first grating element 104A and second grating element 104B. The heel panel element can allow for a user wearing high heels to stand upon the grating element 104A or grating element 104B mitigating a risk that a heel portion of a high heel shoe is caught in between the spacing of the grating.

Furthermore, the heel panel element can be removed (e.g., using screwdriver or hex wrench) such that other shoes can have the heel portion exposed to the ultraviolet light that would previously be blocked from emission through the grating spaces by the heel panel element. In another non-limiting embodiment, the heel panel can be a structure built into first grating element 104A and second grating element 104B such that the area around the heel is not structured as grating but rather as a solid surface for placing the heel. As such, non-limiting embodiments can include a removable heel panel or a heel panel that integrates with the grating of the device itself (e.g., a monolithic part of the grating that isn't removable). Also in an aspect, first grating element 104A and second grating element 104B can include any of a variety of materials such as a composite material made from plastic.

In another aspect, system 100A can include a top plate element 106 comprising support for first grating element 104A and second grating element 104B. For instance, top plate element 106 can include two cutout regions (e.g., rectangle or other shapes) configured to allow ultraviolet light to penetrate through the top plate element 106 and ultimately through first grating element 104A and second grating element 104B that can sit atop top plate element 106.

In a non-limiting embodiment, first grating element 104A and second grating element 104B can be mounted on top of top plate element 106 and screwed or fastened into the top surface of top plate element 106. In one or more non-limiting embodiments, first grating element 104A and second grating element 104B can sit within the cutout region of top plate element 106 or on ledges within the cutout region of top plate element 106 and fastened, snapped, screwed, linked, and/or integrated into top place element 106 by any of a variety of linking mechanisms.

In another embodiment, top plate element 106 can be configured to support and act as a mounting location for a hinge assembly that connects the top covering element 102 to bottom covering element 120. In an aspect, the hinge assembly can facilitate an opening and closing of top covering element 102 to expose or cover the inner elements of system 100A. In another aspect, top covering element 102 can integrate with one more system 100A elements, including but not limited to, reciprocating drive element 108, first brush frame 112A, second brush frame 112B, first grating element 104A, second grating element 104B, top covering element 102, first brush guide 114A, second brush guide 114B, third brush guide 114C, and/or fourth brush guide 114D.

In a non-limiting example embodiment, top plate element 106 can be comprised of a range of one or more metallic material of a sufficient strength and stiffness to provide support and load bearing capabilities consistent with the first grating element 104A and second grating element 104B need and ability to support a user wearing footwear items. In another non-limiting embodiment, top plate element 106, first grating element 104A and second grating element 104B can be combined into one monolithic part (rather than separate interlocking components).

In another embodiment, system 100A can include a reciprocating drive element 108 that facilitates a generation of a brushing and/or sweeping motion of the first brush strips 110A and/or second brush strips 110B. Accordingly, reciprocating drive element 108 enables a brushing and sweeping of debris from the lower surface of the footwear item. In an aspect, reciprocating drive element can comprise a motor (e.g., gear motor 108D), a cam lever (e.g., cam lever 108C), a motor mount (e.g., motor mount 108B), a connecting rod (e.g., connecting rod 108A), and/or a brush drive mount 108E. In an aspect, gear motor 108D can include a direct current (e.g., 12Volt DC motor) or alternating current gear motor that can turn cam lever 108C to facilitate a translation of a rotational motion generated from gear motor 108D into a linear motion of the brushes (e.g., sweeping, back and forth motion).

Also, in an aspect, motor mount 108B can facilitate the mounting of the motor to the entire assembly (comprising the above listed components that makeup the reciprocating drive element 108). In another aspect, connecting rod 108A can be configured to connect with second brush guide 114B and third brush guide 114C via a brush drive mount 108E. In an aspect, brush drive mount 108E can be a mounting panel that acts as a bridge between reciprocating drive element 108 and second brush guide 114B and third brush guide 114C. Furthermore, in an aspect, motor mount 108C can connect the reciprocating drive element 108 to top covering element 102. Accordingly, the motor mount 108C and brush drive mount 108E connect the reciprocating drive element 108 to the top covering element 102 and the brush guides respectively. In one or more non-limiting embodiment, the reciprocating drive element 108 can be adjusted to move different size loads (e.g., different weight brush assemblies) and accommodate variables such as load mass differentiation, mass orientation, move distance requirements, dwell time, move profile, rotary to linear conversion metrics, load support metrics, drive architecture, shaft torque requirement to accelerate a load of the brush assembly, drive control requirements, and/or power supply requirements.

In an aspect, gear motor 108D can be any of a variety of motors such as a gear motor, a DC-stepper motor, a DC-brush servomotor, and/or a DC-brushless servomotor. In another aspect, a component can hold together the assembled elements that comprise the reciprocating drive element 108. In another aspect, reciprocating drive element 108 can be comprised of materials including plastic and metallic parts. In other non-limiting embodiments, the motion generating element of system 100A can take the form of a ball screw and linear guide assembly, a screw and linear guide assembly, a timing belt assembly, a chain with pulley assembly, and/or a manual crank assembly. Accordingly, system 100A can include any one or more mechanisms to facilitate and/or generate a motion of the brush assemblies thus creating a sweeping or brushing motion against the bottom surface of a footwear item.

In another embodiment, system 100A can include first brush strips 110A and second brush strips 110B configured to contact a footwear item to remove debris and/or contaminants. In an aspect, first brush strips 110A and second brush strips 110B can include a base portion with brush bristles protruding from each base portion. In an aspect, first brush strips 110A and second brush strips 110B can include several brush strips spaced apart and configured to allow for the brushes to protrude through the spaces between first grating element 104A and second grating element 104B. In an aspect, the brush strips can comprise bristles such as hair-like bristles, wire bristles, or other varieties of bristles or filaments configured to effectively remove debris, particles and other contaminants from the bottom portion of a footwear item.

In an aspect, first brush strips 110A and second brush strips 110B can be configured for easy installation due to the ability of the brush strip assembly to integrate with first grating element 104A, second grating element 104B, first brush frame 112A and second brush frame 112B. For instance, first brush strips 110A can interlock or be integrated as a monolithic piece with first brush frame 112A. As such, in a non-limiting embodiment, first brush strips 110A can be mounted onto first brush frame 112A. Furthermore, a motion applied to first brush frame 112A can be transferred and/or applied to first brush strips 110A such that a back and forth brushing motion occurs.

Furthermore, in one or more non-limiting embodiments, first brush strips 110A and second brush strips 110B can be configured in various design options, (e.g., the brush strips can conform to contours, shapes, and other variations to allow for the most area contact between the brushes and the footwear item as well as perform the most efficacious brushing away of contaminants. In other embodiments, the brush strip weights can be adjusted (e.g., lower or higher) to allow for the use of the brushes in weight-dependent applications (e.g., heavier and more durable bristles required for brushing away debris from within tread on the bottom of work boots or other heavy-duty footwear items). In yet another aspect, the density of the bristles can be adjusted on the first brush strips 110A and/or second brush strips 110B in order to allow for the greatest area of contact to be made between bristles and the footwear item.

For instance, a greater density of bristles can be utilized in order to minimize the number of gaps between the brushes and the footwear item surface such that the sweeping contacts all or substantially all of the lower surface of the footwear item. In other aspects, the brushes and bristles can be utilized with few metal parts to avoid corrosion and improve chemical resistance of a first brush strips 110A and/or a second brush strip 110B in some embodiments. In another aspect, first brush strips 110A and/or second brush strips 110B can be less bulky and lighter weight in order to facilitate shipping and transportation of such brushes. In an aspect, first brush strips 110A and second brush strips 110B can be changed or removed from first brush frame 112A and second brush frame 112B in order to clean the brush strips or replace them with new unused brush strips. In a non-limiting embodiment, the removable and re-attachable configuration of first brush strip 110A and second brush strip 110B can provide several options for allowing system 100A to operate optimally (e.g., perform the most efficacious brushing, utilize brushes with optimal strength and durability, change out brushes if they become overloaded with too much debris, clean brushes on a regular basis to remove residual debris remaining on the bristles, etc.).

In another aspect, the first brush strip 110A and second brush strip 110B can vary in dimensions (e.g., bristle diameter, bristle length variants, bristle strength, etc.) and material composition. For instance, soft leather shoes may require a softer bristle to be utilized in case the bristles run alongside the side surfaces of the footwear item in addition to the lower surface (e.g., sole) of the footwear item. In some non-limiting embodiments, the bristles can be comprised of natural (e.g., horse hair, animal hair, goat hair, Tampico, hog bristle, etc.) or synthetic bristles (e.g., nylon, polyamides, plastic, taklon, carbon, fiver, coco fiber, polyester, polypropyle, etc.). For instance, in a non-limiting embodiment, nylon can be utilized as a tough and durable synthetic filament that does not shed and has strong abrasive resistance properties which is efficacious for cleaning and scrubbing against footwear surfaces. Furthermore, nylon does not scratch most surfaces, has a high degree of durability, is resistant to most common chemicals and has excellent bend recovery properties such that it doesn't lose its efficacious properties.

Furthermore, the dimensions of first brush strip 110A and second brush strip 110B can be configured to be longer, shorter, and/or have greater or less spacing between brush strips. In another embodiment, the first brush strip 110A and second brush strip 110B can be comprised of materials such as metal, plastic, and/or wood to allow for different weights, ranges of motion, and durability. Furthermore, in an aspect, the brush filaments in each brush strip can be either crimped or straight. In another aspect, the brush ends of the bristles can be flagged (e.g., split, bushy ends) or unflagged depending on the footwear item and surface being cleaned. In yet another aspect, a bristle stiffness and dimensions can be mixed or varied in any of several combinations to improve functionality of the brushing mechanism of system 100A based on the type of footwear item and surface being cleaned.

In another aspect, system 100A can employ first brush frame 112A and second brush frame 112B to create a platform for the first brush strips 110A and second brush strip 110B to be mounted upon. Furthermore, in an aspect, brush frame 112A and brush frame 112B can translate the reciprocating motion (e.g., generated by reciprocating drive assembly 108) to the first brush strips 110A and second brush strips 110B such that the brush strips generate a back and forth brushing motion. In an aspect, first brush frame 112A and second brush frame 112B can be configured to be one single element connected by central metal portion. For instance, brush drive mount 108E can be mounted and connected to both brush frame 112A and second brush frame 112B at the central metal portion.

In another aspect, first brush frame 112A and second brush frame 112B can be configured to connected to other system 100A elements including, but not limited to, first brush strips 110A, second brush strips 110B, reciprocating drive assembly 108, first brush guide 114A, second brush guide 114B, third brush guide 114C, fourth brush guide 114D, first grating element 104A, second grating element 104B, and top plate element 106. For instance, in a non-limiting embodiment, a screw can be driven through guide holes in brush drive mount 108E, second brush guide 114B, first brush frame 112A, top plate element 106, and first grating element 104A thus integrating all such elements of system 100A.

In another aspect, first brush frame 112A and second brush frame 112B can be configured to support brush strips (e.g., first brush strips 110A and second brush strips 110B) such that the strips don't bend, bow or flex when static or moving. As such, first brush frame 112A and/or second brush frame 112B can be comprised of a variety of materials such as metallic or plastic. In yet another non-limiting embodiment, the first brush material can be comprised of a composite material. Furthermore, in another non-limiting embodiment, the first brush frame 112A and second brush frame 112B can be integrated with brush strips (e.g., first brush strips 110A and second brush strips 110B) to form a single component part without moving components to further reduce any friction created between moving parts.

In another aspect, system 100A can employ first brush guide 114A, second brush guide 114B, third brush guide 114C, and fourth brush guide 114D, wherein each brush guide can be connected to the set of brush strips (e.g., first brush strip 110A and second brush strip 110B), and wherein the first brush guide 114A and the second brush guide 114B are connected to a first brush strip 110A, and wherein the third brush guide 114C and the fourth brush guide 114D are connected to a second brush strip 110B. In an aspect, the brush guides can facilitate a smooth movement of the brush assembly. For instance, the motion generated by the reciprocating drive 108 can transfer to brush second brush guide 114B and third brush guide 114C which can be connected to the brush drive mount 108E. As such the motion can cause the first brush guide 114A, second brush guide 114B, third brush guide 114C, and fourth brush guide 114D to move forward and back which can result in a brushing or sweeping motion of first brush strip 110A and/or second brush strip 110B back and forth thus brushing away debris with the brush bristles from the lower surface of a footwear item.

In a non-limiting embodiment, the first brush guide 114A, second brush guide 114B, third brush guide 114C, and fourth brush guide 114D can integrate with lower frame 118, or first brush frame 112A and second brush frame 112B. For instance, a screw can pass through guide holes within brush frame 112A and then into second brush guide 114B. Also, in another non-limiting embodiment, a screw can pass through lower frame 118 and then into guide holes within first brush frame 112A and then into second brush guide 114B. In another aspect, a screw can pass through brush frame 112A and then into first brush guide 114A. Similarly, third brush guide 114C and fourth brush guide 114D can be configured to integrate with brush frame 112B via a screwing, interlocking, snapping or other integrative mechanism.

In another aspect, the other brush guides can also be integrated with at least some of the other system 100A elements disclosed herein. In yet another aspect, first brush guide 114A, second brush guide 114B, third brush guide 114C, and fourth brush guide 114D can be comprised of any of a variety of materials such as metal or plastic materials.

In other embodiments, one or more brush guide can be comprised of metal, plastic or composite material. In another aspect, the first brush guide 114A, second brush guide 114B, third brush guide 114C, and fourth brush guide 114D can be configured to allow for minimum friction between component parts of system 100A (e.g., such as between reciprocating drive assembly 108, first brush frame 112A, first brush strips 110A, and other such components). In another aspect, the brush guides can be configured to provide optimal guidance to the first brush frame 112A and second brush frame 112B as well as the first brush strips 110A and second brush strips 110B. As such, brush guides facilitate a smooth and fluid back and forth brushing motion ensues by the brush strips.

In another aspect, system 100A can employ first light assembly 116A and second light assembly 116B. In an aspect, first light assembly 116A and second light assembly 116B can be configured to emit light such as ultraviolet light on the lower surface of a footwear item in order to decontaminate the portion of the footwear item exposed to the ultraviolet light emissions. For instance, germicidal wavelengths (e.g., between 200 to 300 nm) of ultraviolet light (e.g., short-wavelength ultraviolet light) can inactivate microorganisms such as bacteria, viruses, and protozoa thus disinfecting the surface of the footwear item against harmful microorganisms that can then spread to environments making contact with the footwear item surface. As such, first light assembly 116A and second light assembly 116B can decontaminate the bottom surface of a footwear item by exposing the surface to disinfecting light emissions such as ultraviolet light.

Furthermore, in an aspect, first brush strips 110A and second brush strips 110B can brush away large debris and contaminants from the surface of the footwear item thus exposing more of the lower surface of the footwear item. In an aspect, first light assembly 116A or second light assembly 116B can disinfect the footwear item from pathogenic organisms (e.g., cholera, polio, typhoid, hepatitis), bacteria, chlorine resistant pathogens (cryptosporidium, giardia, etc.), viruses, parasites, fungi, yeasts, algae, chemical contaminants (e.g., pesticides, industrial solvents, pharmaceuticals, etc.), and other contaminants. In an aspect, first light assembly 116A can comprise florescent tubes capable of emitting ultraviolet C-band light. In one or more embodiment, the wattage of the fluorescent tubes can be varied. For instance, in a non-limiting embodiment, the florescent tubes can be between 10-40 watts.

In one or more embodiments, the length of exposure of the lower surface of the footwear item can be varied to bring about the most efficacious disinfection results. For instance, in a non-limiting embodiment the exposure of the surface of the footwear item can be five second exposure. In another one or more embodiments, the distance at which the first light assembly 116A and second light assembly 116B are positioned apart from the lower surface of the footwear item can be varied. For instance, in a non-limiting embodiment the distance between the first light assembly 116A and the lower surface of the footwear item can be three inches. In other non-limiting embodiments, the ultraviolet light can be emitted from any of several ultraviolet light sources such as a germicidal lamp (e.g., low pressure lamp, high pressure lamp, etc.), light emitting diode (LED). Furthermore, in an aspect, first light assembly 116A and second light assembly 116B can include a ballast that allows for the regulation of current to flow through the ultraviolet light source (e.g., lamp, bulb, tube, etc.).

In another aspect, the electrical ballast can limit the amount of current that flows to the ultraviolet light source. Accordingly, system 100A can allow for the ultraviolet light wavelength to be tuned to various wavelengths to match the most effective wavelength for disinfection under a wide range of environmental conditions (e.g., variations in temperature, humidity, air pressure, etc.). As such, system 100A can allow for the capability to adjust light emission wavelengths emitted from first light assembly 116A and second light assembly 116B to increase the efficiency of a wide range of contaminant inactivation. Furthermore, other embodiments of system 100A can allow for the adjustment of power applied to the light assemblies as well as adjustments to exposure times and/or light intensities emitted in order to impact decontamination efficacies.

In another embodiment, first light assembly 116A and second light assembly 116B can integrate with lower frame 118. For instance, the ballast or holder of the ultraviolet light source can clip, snap, screw or integrate in another manner into the base of lower frame 118. In one or more non-limiting embodiments, the manner of integration (e.g., snapping, clipping, etc.) can be adjusted upwards or lower to reconfigure the distance between the ultraviolet emission source and the lower surface of the footwear item. In yet another aspect, the ultraviolet light emitted from the first light assembly 116A and the second light assembly 116B can be emitted through the first grating element 104A and second grating element 104B and ultimately contact a lower surface of a footwear item.

In those regions where the ultraviolet light emission does not contact the footwear item, the light emission contacts the awning of top covering element 102. As such, a user is protected from being exposed to the ultraviolet light emission by such awning. In one or more other non-limiting embodiments, the awning of top covering element 102 can protrude further horizontally to cover the area above each respective first grating element 104A and second grating element 104B and leaving a cutout region (e.g., semicircular region) by which can circumscribe a user ankle or leg region. Accordingly, any ultraviolet light emissions that pass through first grating element 104A and second grating element 104B that don't contact the lower surface of the footwear item can make contact with the elongated awning portion of top covering element 102. In yet another aspect, the ultraviolet light emissions can penetrate beyond the first brush strips 110A and second brush strips 110B because the brush strips move back and forth during the brushing motion to allow light to pass unblocked (e.g., a first movement unblocks a first region and then a second movement unblocks a second region during at which time ultraviolet light penetrates beyond the brush strips).

In another non-limiting embodiment, above the grating element (e.g., first grating element 104A and second grating element 104B) can be a containment element configured to receive a footwear item within four walls of the containment element. In an aspect, the containment element can be connected to (as an extension of the interior of the containment element) or allow for a shroud comprising one or more bristles protruding from one or more of the inside walls of the shroud to be inserted within the containment element. The floor of the shroud can be the grating elements (e.g., first grating element 104A and second grating element 104B). As such, a shroud can be located or positioned on top of each respective grating element. In a non-limiting embodiment, the shroud can be integrated onto the grating elements (e.g., snapping, clipping, magnetized, etc.). In another non-limiting embodiment, the shroud can be formed as a monolithic piece of the top plate element 106.

The shroud can have four walls (e.g., stiff walls, elastic walls, flexible walls, rigid walls, etc.) where each wall helps encapsulate a footwear item such as a shoe and the bristles nestle around the shoe. Furthermore, in an aspect, the shroud can sit on top of the grating element while cleaning of the bottom of the footwear item occurs. In another aspect, ultraviolet light cannot escape beyond the bottom of the footwear item and the protruding bristles of the shroud thus blocking ultraviolet light from contacting a person. Additionally, the protruding bristles can serve to clean a footwear item around the sides.

In one or more embodiment, system 100A can also employ lower frame element 118. In other embodiments, lower frame element 118 is absent from system 100A. In an aspect, the lower frame 118 can be configured to create a structure for the bottom covering element 120 and other internal components of system 100A to mount or bolt into. In one or more embodiment, lower frame 118 can integrate with first light assembly 116A and second light assembly 116B, top covering element 102, and/or bottom covering element 120. In an aspect, lower frame 118 can be comprised of a metallic material and in a non-limiting embodiment can be configured to support a weight of between 300-400 pounds. In another non-limiting embodiment, lower frame 118 can be comprised of a plastic material, a composite material, and/or other such materials. Furthermore, in an aspect, in embodiments absent lower frame 118, system 100A elements such as first light assembly 116A and second light assembly 116B, and/or top covering element 102 can be integrated with bottom covering element 120.

In another embodiment, system 100A can employ bottom covering element 120 configured to provide structural support to system 100A elements as well as additional external weight (e.g., from a user standing on the grating elements wearing footwear items). Furthermore, in an embodiment, bottom covering element 120 can be configured to enclose and protect system 100A internal elements and components by creating an outer protective shell. In another non-limiting embodiment, bottom covering element 120 can integrate with lower frame 118 (e.g. in embodiments that utilize such lower frame 118). Furthermore, in one or more embodiments, bottom covering element 120 can include various materials such as plastic and nylon. In another aspect, the bottom covering element 120 can include features such as mounting lights, wires (detached and/or attached), electrical components, a region that holds a charging port, a region that secures batteries, detachable feet, and/or fixed feet (e.g., wheels, legs, etc.). In yet another aspect, bottom covering element 120 can support weight of system 100A components and/or external items imposed on system 110A (e.g., weight of a standing user). In another non-limiting embodiment, bottom covering element 120 can be absent and in its place a metal formed plate can be utilized to support the all other system 100A component assemblies. Similarly, in one or more embodiment, in lieu of bottom covering element 120 can be configured a machined frame or a welded metal frame.

In yet another embodiment, system 100A can employ weight sensor 122 configured to receive weight data based on a force applied system 100A (e.g., applied to first grating element 104A and second grating element 104B). In an aspect, a logic controller can be connected to weight sensor 122 and configured to ensure that a threshold weight requirement is satisfied prior to activation of system 100A cleaning and disinfecting operations. In an aspect, weight sensor 122 can receive weight data representing a weight applied to system 100A and if a value associated with such weight data is greater than a threshold value then system 100A can activate and the cleaning and disinfecting mechanism can commence. For instance, if the weight threshold for activation is 10 pounds and the data received by weight sensor 122 represents a weight of 5 pounds, then system 100A can remain deactivated. However, in another instance, if weight sensor 122 receives weight data representing one hundred and fifty pounds then the threshold weight requirement is satisfied and the cleaning and disinfecting operations commence.

In an aspect, weight sensor 122 can integrate with bottom covering element 120 and first brush frame 112A and second brush frame 112B. In another aspect, weight sensor 122 can be configured to generate a magnitude of DC voltage that is proportional to pressure applied to system 100A (e.g., first grating element 104A and second grating element 104B). Furthermore, in an aspect, weight sensor 122 can be configured to provide a means of conveying a direct current (DC) signal (e.g., using a wire). In one or more alternative embodiment, a mechanical device can be activated based on a required weight being determined to be satisfied with a wireless signal output. In one or more other non-limiting embodiment, no sensor may be utilized but instead a mechanical device (e.g., a button or switch) or other non-mechanical device (e.g., a wireless device) can indicate that it is safe to operate the device. Accordingly, the weight sensor 122 can convert a load force that is detected to act upon system 100A (or system 100A components such as a grid component) and convert such load force into an electronic signal. Furthermore, the applied force or load to weight sensor 122 can change the resistance of weight sensor 122 and thus change an output voltage of the logic controller based on an application of an input voltage.

In an aspect, system 100A can be utilized in an initial setup by a user plugging in a wall power brick into household outlet (e.g., a 110 VAC outlet). Furthermore, the user can plug the power brick into a system 100A and subsequently turn a power switch component that is part of system 100A to the "on" position. In another aspect, a user can stand on a first grating element 104A and second grating element 104B. In an aspect, system 100A can check for the presence of an adult user by determining by weight sensor 122 that a threshold weight is satisfied. If an adult user meeting or overcoming the threshold weight is standing on system 100A grating elements, then the cleaning and disinfecting operations can commence.

For instance, system 100A can activate reciprocating drive assembly 108 such that motor mount 108B generates a rotating motion and connecting rod 108 as well as cam lever element 108C convert the rotating motion into a back and forth movement to drive cleaning of the user shoes by a brushing mechanism. As such, the first brush strips 110A and second brush strips 110B begin to brush the bottom surface of the left and right shoes. Furthermore, in another aspect, a relay can be tripped (e.g., by components of system 100A such as reciprocating drive assembly 108) that results in the ultraviolet lights of first light assembly 116A and second light assembly 116B to emit lights in order to disinfect the lower surface of the user shoes. In an aspect, the ultraviolet light emission can occur simultaneously, subsequent to, or prior to the brush cleaning mechanism incurred by first brush strips 110A and second brush strips 110B.

In an aspect, the first light assembly 116A and second light assembly 116B as well as first brush strips 110A and second brush strips 110B can perform its disinfecting operations and cleaning operations respectively for a determined time based on a programmed code. In an instance, the programmed code can represent a set of electronic instructions that a microcontroller (e.g., microcontroller 124) executes (e.g., using a processor employed by the microcontroller). In an aspect, system 100A can also include system components that execute microcontroller implemented instructions. In an aspect, such instructions can employ commands that determine whether or not a weight threshold is satisfied, the duration or length of time of cleaning operations (e.g., running the brush strips), the duration or length of time to perform disinfecting operations (e.g., how long and when to trigger the emission of ultraviolet lights), and other such operations. In an aspect, the system instructions can be executed or not executed based on data received from sensors such as weight sensor 122. In another aspect, microcontroller 124 is a component of system 100A that can convert instructions executed by the processor into signals for transmission or receipt through one or more pin.

In an aspect, based on the termination of period of time specified by the coded instructions, the reciprocating drive assembly 108 deactivates (e.g., stops operating or powers down), the light relay (that was tripped) deactivates resulting in first light assembly 116A and second light assembly 116B stopping its emission of (ultraviolet) light. As such, system 100A completes its cleaning and disinfecting run cycle and based on a user stepping off of the first grating element 104A and second grating element 104B, the system 100A components reset in anticipation of performing operations for another user. In a non-limiting embodiment, system 100A can also operate to allow for user wearing high heels to utilize the cleaning and disinfecting operations. In such instance, a user can place the shoe toe of the high heel on first grating element 104A and second grating element 104B while also adjusting the high heel portion of the shoe to sit in a heel plate portion of grating element 104A and grating element 104B respectively. Accordingly, each high heel can be stabilized within the plate portion of the grating elements in order to preclude any slipping, falling, or knock-down of the high heel. By creating the stable environment, the heel plate allows users wearing a variety of footwear to be disinfected and cleaned.

Figure 1B:
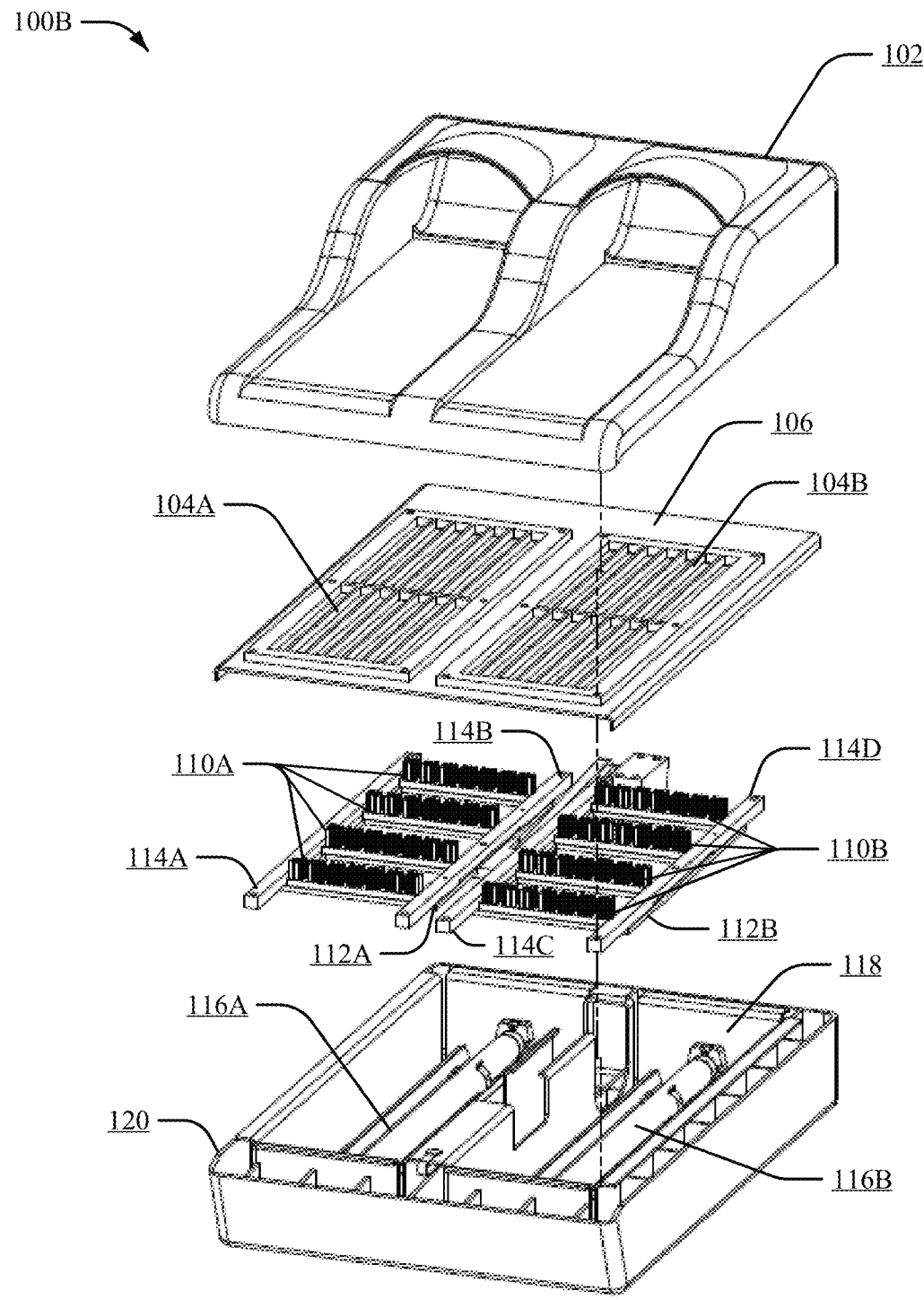
FIG. 1B illustrates an exploded view of a vertical arrangement of some of the components of an example non-limiting system for disinfecting a contaminated item in accordance with one or more implementation described herein.

Turning now to FIG. 1B, illustrated is an exploded view of a vertical arrangement of some of the components of an example non-limiting apparatus 100B for disinfecting a contaminated item in accordance with one or more implementation described herein. Repetitive description of like elements employed in other embodiments described herein is omitted for sake of brevity. In an aspect, system 100B (e.g., a different perspective view of system 100A) illustrates top covering element 102, first grating element 104A, second grating element 104B, top plate element 106, first brush strips 110A, second brush strips 110B, first brush frame 112A, second brush frame 112B, first brush guide 114A, second brush guide 114B, third brush guide 114C, fourth brush guide 114D, first light assembly 116A, second light assembly 116B, lower frame 118, and bottom covering element 120.

In an aspect, system 100B illustrates, by the exploded view, the integration of several components of system 100B (and system 100A) in a non-limiting embodiment. In an aspect, several of the elements are illustrated with screw hole configurations in order to indicate regions where screws can be inserted in order to integrate such component parts. Furthermore, in an aspect, a hashed line can be viewed extending from a corner of top covering element 102 through a screw hole of second grating element 104B, through another screw hole in top plate element 106, through a screw hole within fourth brush guide 114D, and into a screw hole located at the corner of lower frame 118 and within bottom covering element 120. As such, in an instance, such elements and components of system 100A can be integrated via screw mechanisms, snapping mechanisms, locking mechanisms, hinge mechanisms, and other integrative mechanisms.

Figure 1C:
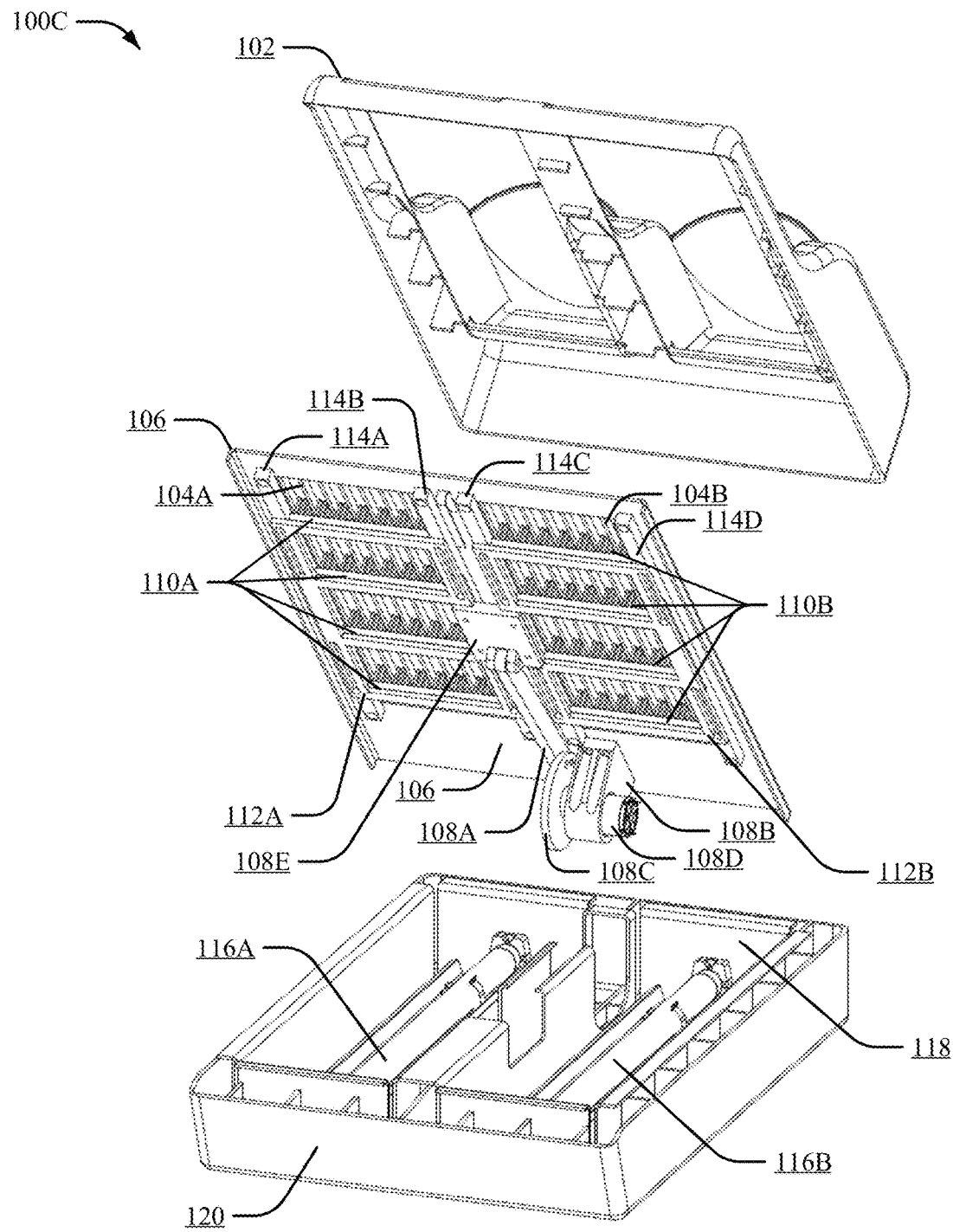
FIG. 1C illustrates another exploded view providing a different vantage point of some of the components of an example non-limiting system for disinfecting a contaminated item in accordance with one or more implementation described herein.

Turning now to FIG. 1C, illustrated is another exploded view providing a different vantage point of some of the components of an example non-limiting system 100C for disinfecting a contaminated item in accordance with one or more implementation described herein. Repetitive description of like elements employed in other embodiments described herein is omitted for sake of brevity. In an aspect, the exploded view of system 100C (a different perspective view of system 100A and system 100B) illustrates the underside of several of the elements of system 100C (and system 100A and system 100B).

In an aspect, system 100C illustrates top covering element 102, first grating element 104A, second grating element 104B, top plate element 106, reciprocating drive assembly 108, connecting rod 108A, motor mount 108B, cam lever element 108C, gear motor 108D, brush drive mount 108E, first brush strips 110A, second brush strips 110B, first brush frame 112A, second brush frame 112B, first brush guide 114A, second brush guide 114B, third brush guide 114C, fourth brush guide 114D, first light assembly 116A, second light assembly 116B, lower frame 118, and bottom covering element 120. As illustrated by system 100C, the underside of top cover element 102 can be configured to provide a cavity portion that can fit (e.g., cutout holes) with elements such as first grating element 104A and second grating element 104B.

Furthermore, in an aspect, the underside perspective view illustrates the manner in which first brush strips 110A and second brush strips 110B fit within the spaces of first grating element 104A and second grating element 104B. In another aspect, system 100C provides a clear viewpoint of reciprocating drive assembly 108. In an aspect, motor mount 108B can be configured to connect (e.g., via screw) into top plate element 106. Furthermore, in an aspect, brush drive mount 108E can be configured to connect with a central portion of first brush frame 112A and second brush frame 112B and further into top plate element 106. In another aspect, the illustration also identifies the mechanism of gear motor 108D to generate a rotational motion, as well as the ability of cam lever element 108C to translate the rotational motion into a back and forth linear motion by its connection with connecting rod 108A.

In an aspect, connecting rod 108A can move back and forth as a result of the cam lever element 108C rotational motion. Furthermore, the back and forth motion from the connecting rod 108A is employed through the brush drive mount 108E, which via its connection to first brush frame 112A and second brush frame 112B transfers the linear motion the brush frames. Accordingly, the first brush frame 112A and second brush frame 112B are connected to first brush strips 110A and second brush strips 110B respectively which result in a linear back and forth brushing motion of the brushes on such brush strips. In another aspect, first light assembly 116A and second light assembly 116B can emit ultraviolet light that passes through first grating element 104A and second grating element 104B.

Figure 1D:
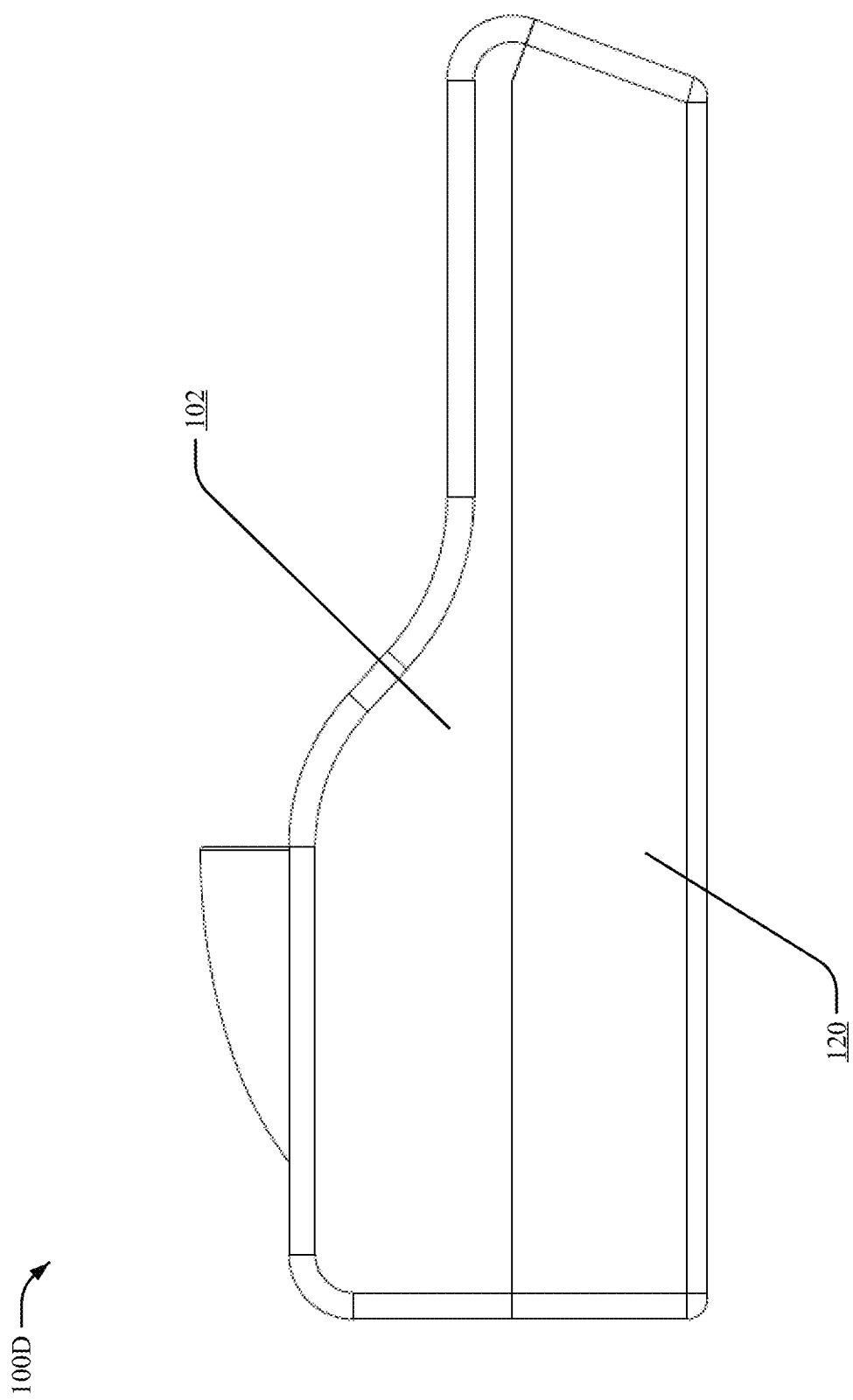
FIG. 1D illustrats an exploded view of a side view of an example non-limiting system for disinfecting a contaminated item in accordance with one or more implementation described herein.

Turning now to FIG. 1D, illustrated is an exploded view of a side view of an example non-limiting system 100D for disinfecting a contaminated item in accordance with one or more implementation described herein. Repetitive description of like elements employed in other embodiments described herein is omitted for sake of brevity. In an aspect, system 100D is a different perspective view of system 100A-C. Furthermore, in an aspect, illustrated from a side view perspective are top covering element 102 and bottom covering element 120. In a non-limiting embodiment both top covering element 102 and bottom covering element 120 are illustrated in a closed manner where they are capable of opening at a hinge in order to expose the internal elements of system 100D (and systems 100A-C). In an aspect, top covering element 102 can be seen with the curved awning portion to protect a user from emitted ultraviolet light exposure in the event ultraviolet light surrounding the toe region of the footwear item emanates beyond the perimeter of the toe area upwards.

Figure 1E:
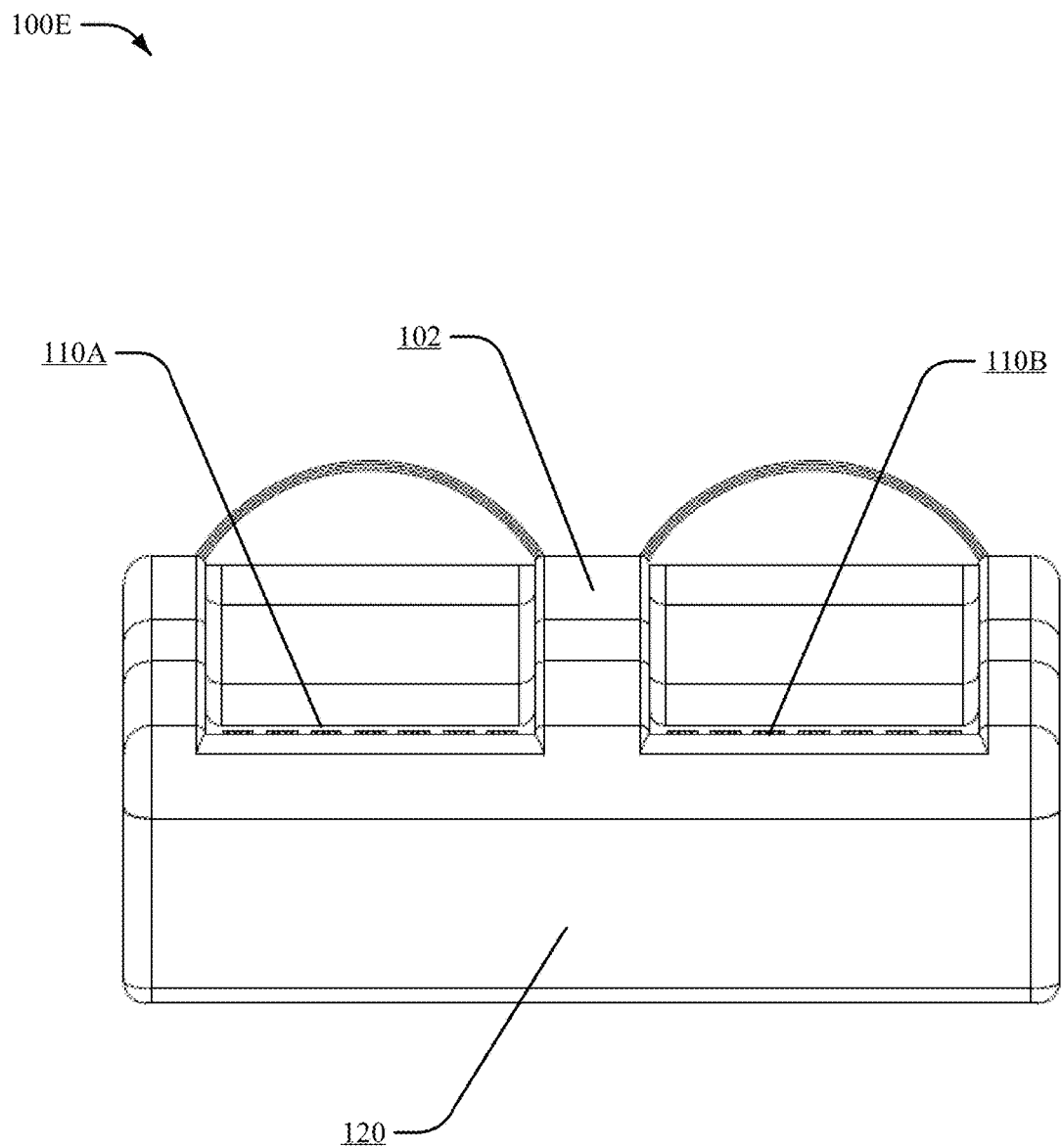
FIG. 1E illustrates a backside view of an example non-limiting system for disinfecting a contaminated item in accordance with one or more implementation described herein.

Turning now to FIG. 1E, illustrated is a backside view of an example non-limiting system for disinfecting a contaminated item in accordance with one or more implementation described herein. Repetitive description of like elements employed in other embodiments described herein is omitted for sake of brevity. In an aspect, system 100E is a different perspective view of system 100A-D. In an aspect, illustrated are top covering element 102 and bottom covering element 120 in a closed position from the back side of the apparatus. In an aspect, the first grating element 104A and second grating element 104B can be viewed as well as the awning portions of top covering element 102.

Turning now to FIG. 1F, illustrated is a top viewpoint providing a perspective view from an aerial vantage point of an example non-limiting system for disinfecting a contaminated item in accordance with one or more implementation described herein. Repetitive description of like elements employed in other embodiments described herein is omitted for sake of brevity. In an aspect, system 100F is a different perspective view of system 100A-E. In an aspect, a viewpoint peering straight down at system 100F is illustrated. Furthermore, in an aspect, system 100F illustrates top covering element 102, first brush strips 110A, second brush strips 110B, first grating element 104A, and second grating element 104B. It is apparent that the bristles of the brushes strips protrude between the spacing in the grating elements. Furthermore, the brush strips can move forward and back to allow for emitted ultravioelt light to contact most or all of the regions of the lower surface of the footwear item.

Figure 1G:
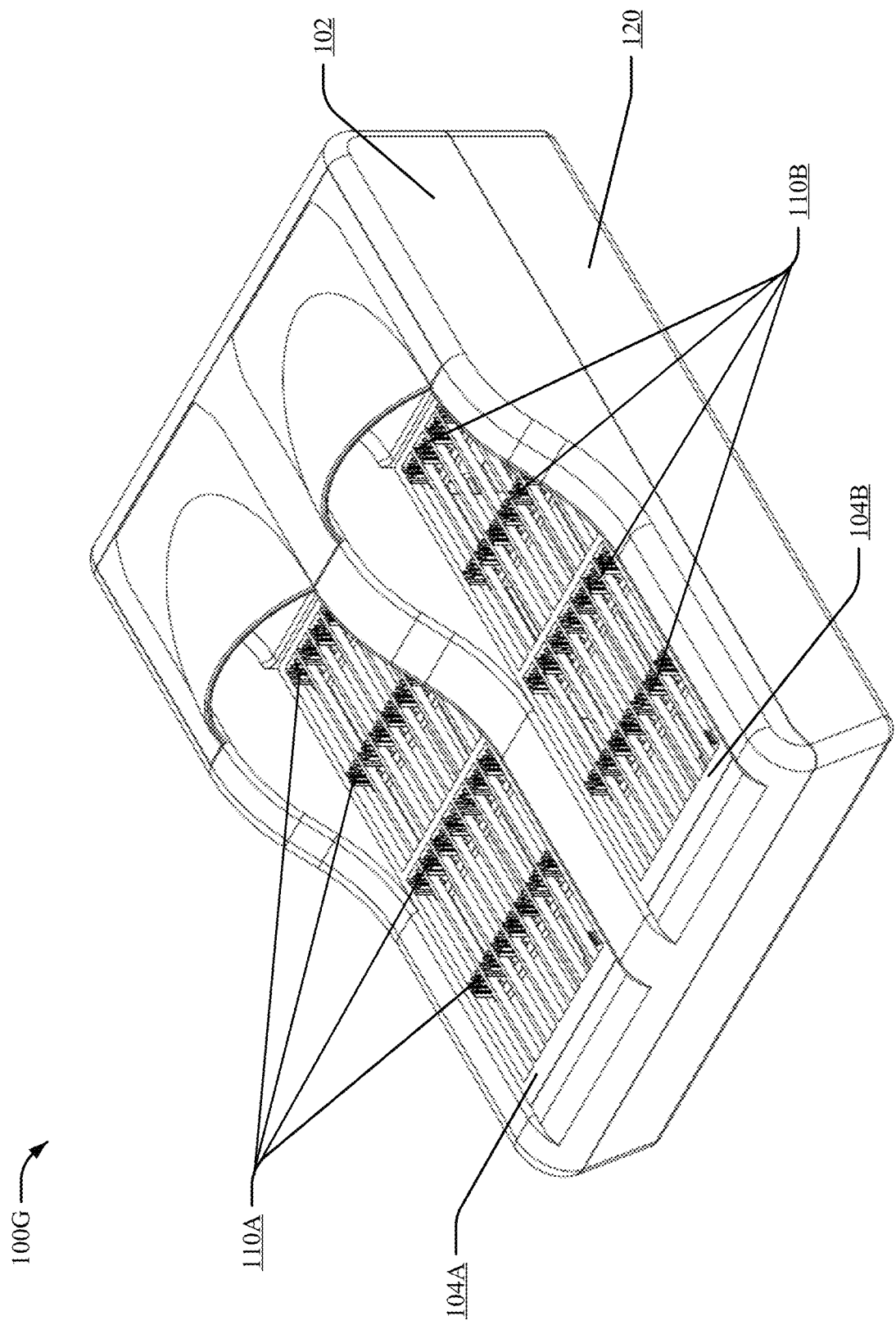
FIG. 1G illustrates a diagonal viewpoint of an example non-limiting system for disinfecting a contaminated item in accordance with one or more implementation described herein.

Turning now to FIG. 1G, illustrated is a diagonal viewpoint of an example non-limiting system 100G for disinfecting a contaminated item in accordance with one or more implementation described herein. Repetitive description of like elements employed in other embodiments described herein is omitted for sake of brevity. In an aspect, system 100G is a different perspective view of system 100A-F. In an aspect, the tilted sideview profile of system 100G illustrates the first brush strips 110A, second brush strips 110B, first grating element 104A, second grating element 104B, top covering element 102, and bottom covering element 120. In an aspect, system 100G makes apparent some of the contours of the apparatus in a non-limiting embodiment. Furthermore, in an aspect, system 100G illustrates the flush nature of first grating element 104A and second grating element 104B within the cutout region of top covering element 102.

Figure 1H:
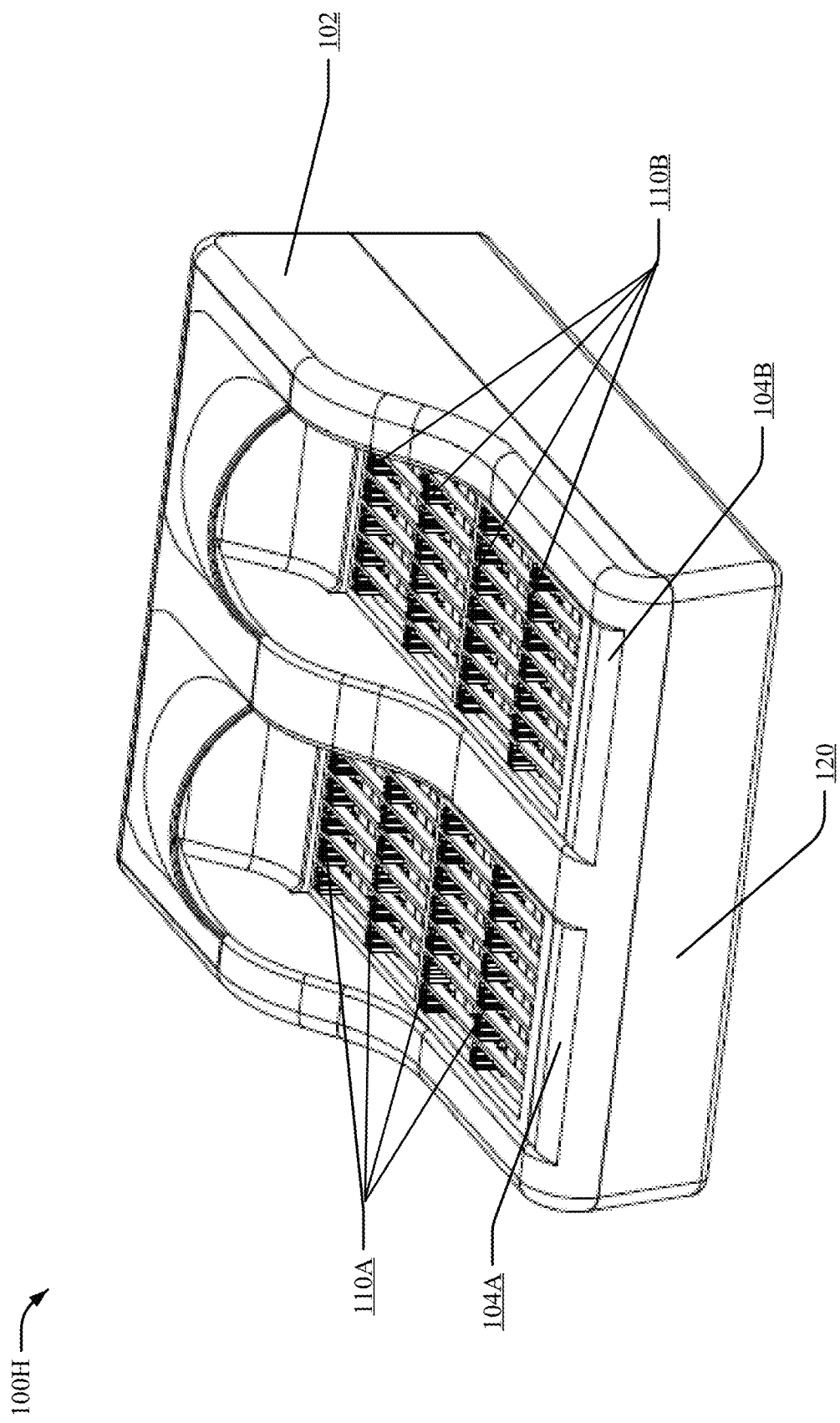
FIG. 1H illustrates another diagonal viewpoint of an example non-limiting system for disinfecting a contaminated item in accordance with one or more implementation described herein.

Turning now to FIG. 1H, illustrated is another diagonal viewpoint of an example non-limiting system for disinfecting a contaminated item in accordance with one or more implementation described herein. Repetitive description of like elements employed in other embodiments described herein is omitted for sake of brevity. In an aspect, system 100H is a different perspective view of system 100A-G. In an aspect, the tilted sideview profile of system 100H illustrates the first brush strips 110A, second brush strips 110B, first grating element 104A, second grating element 104B, top covering element 102, and bottom covering element 120. In an aspect, system 100H makes apparent some of the contours of the apparatus in a non-limiting embodiment. Furthermore, in an aspect, system 100G illustrates the flush nature of first grating element 104A and second grating element 104B within the cutout region of top covering element 102.

Turning now to FIG. 1I, illustrated is a side view point of an example non-limiting system for disinfecting a contaminated item in an open position in accordance with one or more implementation described herein. Repetitive description of like elements employed in other embodiments described herein is omitted for sake of brevity. In an aspect, system 100I is a different perspective view of system 100A-H. In an aspect, system 100H illustrates top covering element 102 ajar and apart from bottom covering element 120. Furthermore, reciprocating drive 108 can be viewed and can be configured to connect with top place element 106. As such, illustrated are connecting rod 108A, cam lever element 108C, and brush drive mount 108E.

Figure 1J:
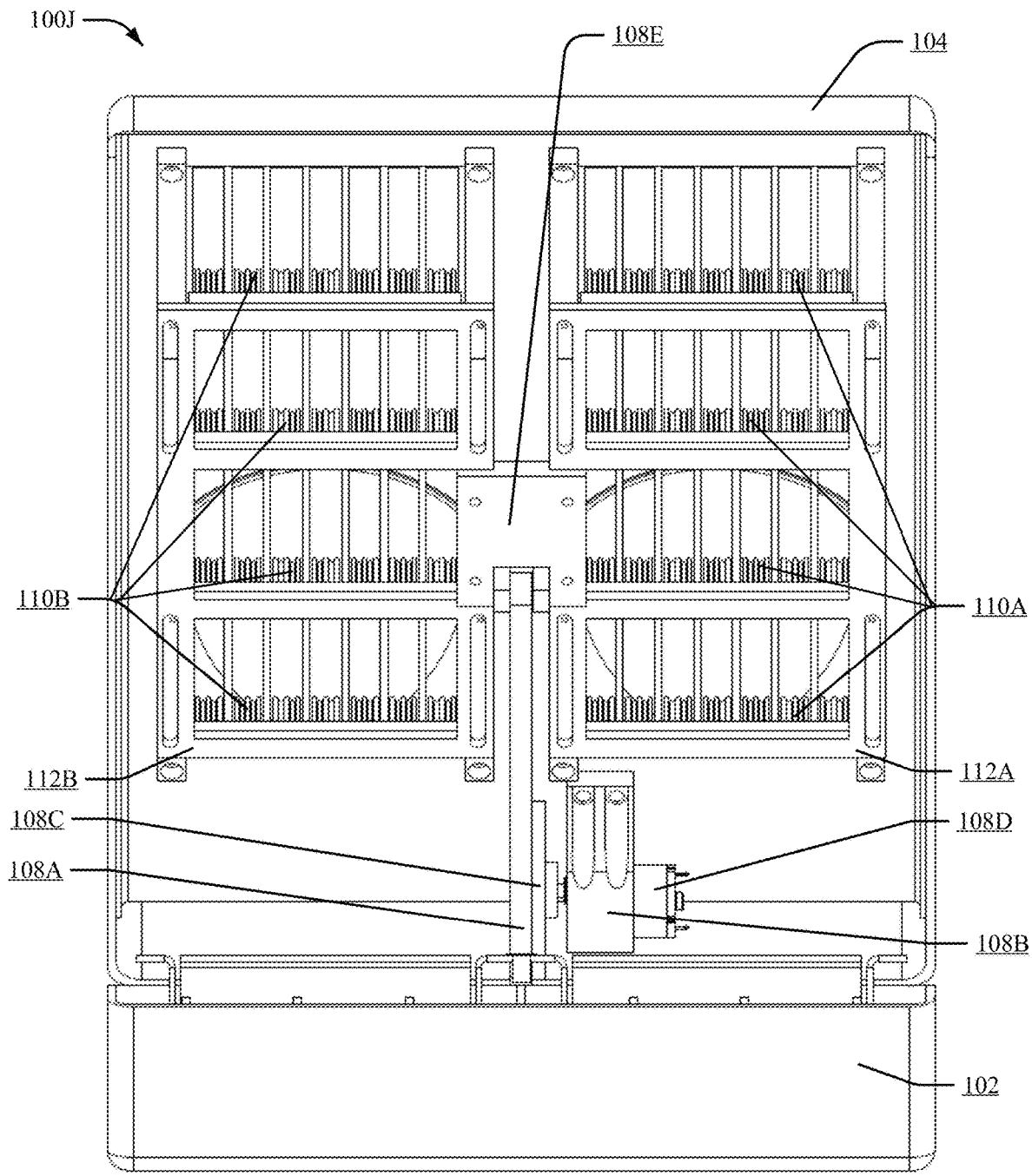
FIG. 1J illustrates an overhead or top view of an example non-limiting system for disinfecting a contaminated item in an open position in accordance with one or more implementation described herein.

Turning now to FIG. 1J, illustrated is an overhead or top view of an example non-limiting system for disinfecting a contaminated item in an open position in accordance with one or more implementation described herein. Repetitive description of like elements employed in other embodiments described herein is omitted for sake of brevity. In an aspect, system 100J is a different perspective view of system 100A-I.

In an aspect, system 100J illustrates top covering element 102, first brush strips 110A, second brush strips 110B, first brush frame 112A, second brush frame 112B, connecting rod 108A, motor mount 108B, cam lever element 108C, gear motor 108D, brush drive mount 108E, bottom covering element 120. In an aspect, the viewpoint presented in system 100J clearly illustrates reciprocating drive assembly 108 and its configuration as a hinge between top covering element 102 and bottom covering element 120.

Figure 1K:
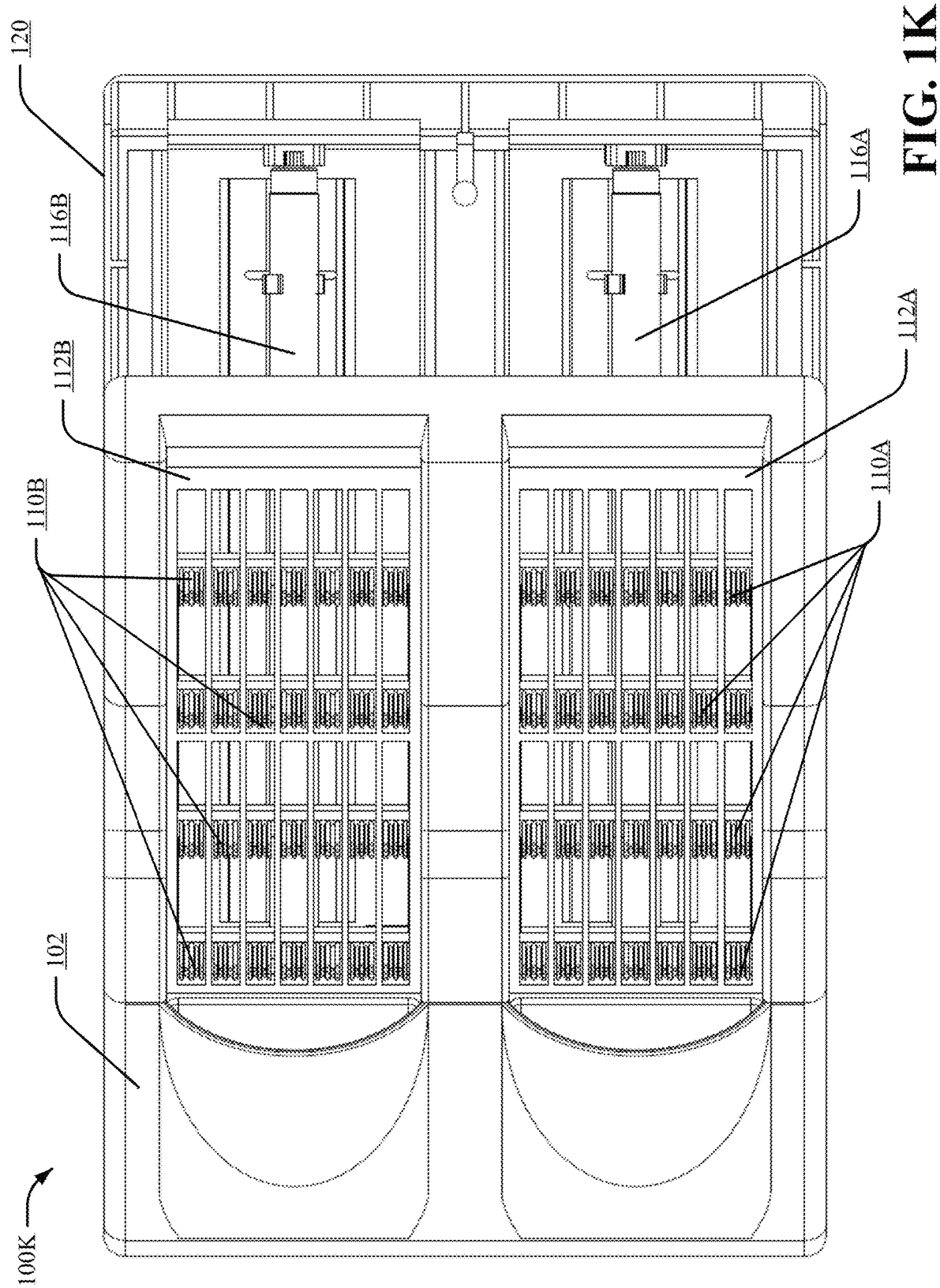
FIG. 1K illustrates an overhead or top view of an example non-limiting system for disinfecting a contaminated item in a partially open position in accordance with one or more implementation described herein.

Turning now to FIG. 1K, illustrated is an overhead or top view of an example non-limiting system 100K for disinfecting a contaminated item in a partially open position in accordance with one or more implementation described herein. Repetitive description of like elements employed in other embodiments described herein is omitted for sake of brevity. In an aspect, system 100K is a different perspective view of system 100A-J.

In an aspect, system 100K illustrates top covering element 102, first brush strips 110A, second brush strips 110B, first brush frame 112A, second brush frame 112B, first light assembly 116A, second light assembly 116B, bottom covering element 120. In an aspect, the viewpoint presented in system 100J clearly illustrates reciprocating drive assembly 108 and its configuration as a hinge between top covering element 102 and bottom covering element 120. In an aspect, top covering element 102 is partially opened thus illustrating the viewpoint of first light assembly 116A and second light assembly 116B seated within lower frame 118.

Figure 1L:
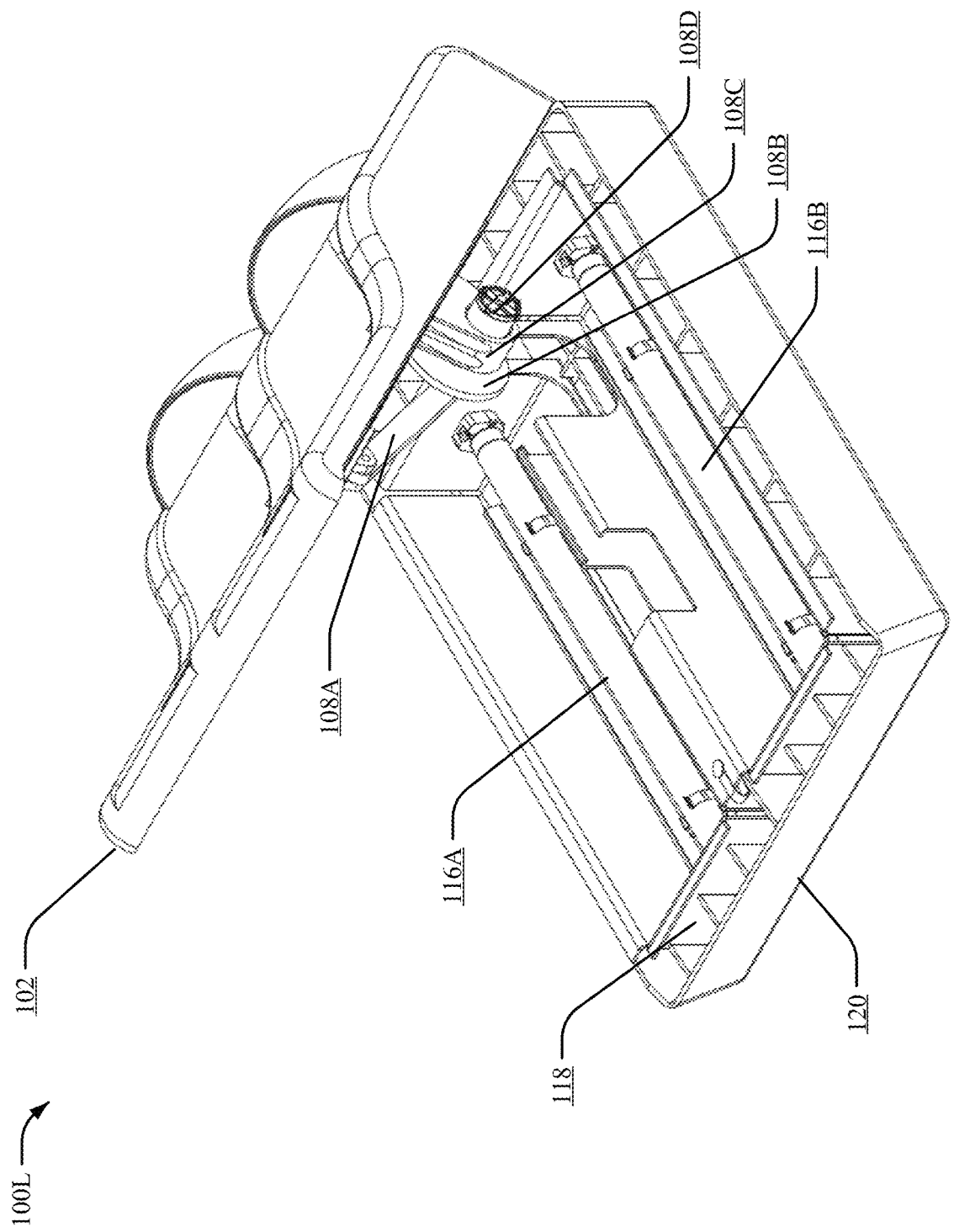
FIG. 1L illustrates a partial side profile view of an example non-limiting system for disinfecting a contaminated item in a partially open position in accordance with one or more implementation described herein.

Turning now to FIG. 1L, illustrated is a partial side profile view of an example non-limiting system 100L for disinfecting a contaminated item in a partially open position in accordance with one or more implementation described herein. Repetitive description of like elements employed in other embodiments described herein is omitted for sake of brevity. In an aspect, system 100L is a different perspective view of system 100A-K. In an aspect, system 100L illustrates top covering element 102, connecting rod 108A, motor mount 108B, can lever element 108C, gear motor 108D, first light assembly 116A, second light assembly 116B, lower frame 118, and bottom covering 120. In an aspect, the components and elements housed within bottom covering 120 are more clearly viewable from the system 100L perspective view.

Figure 1M:
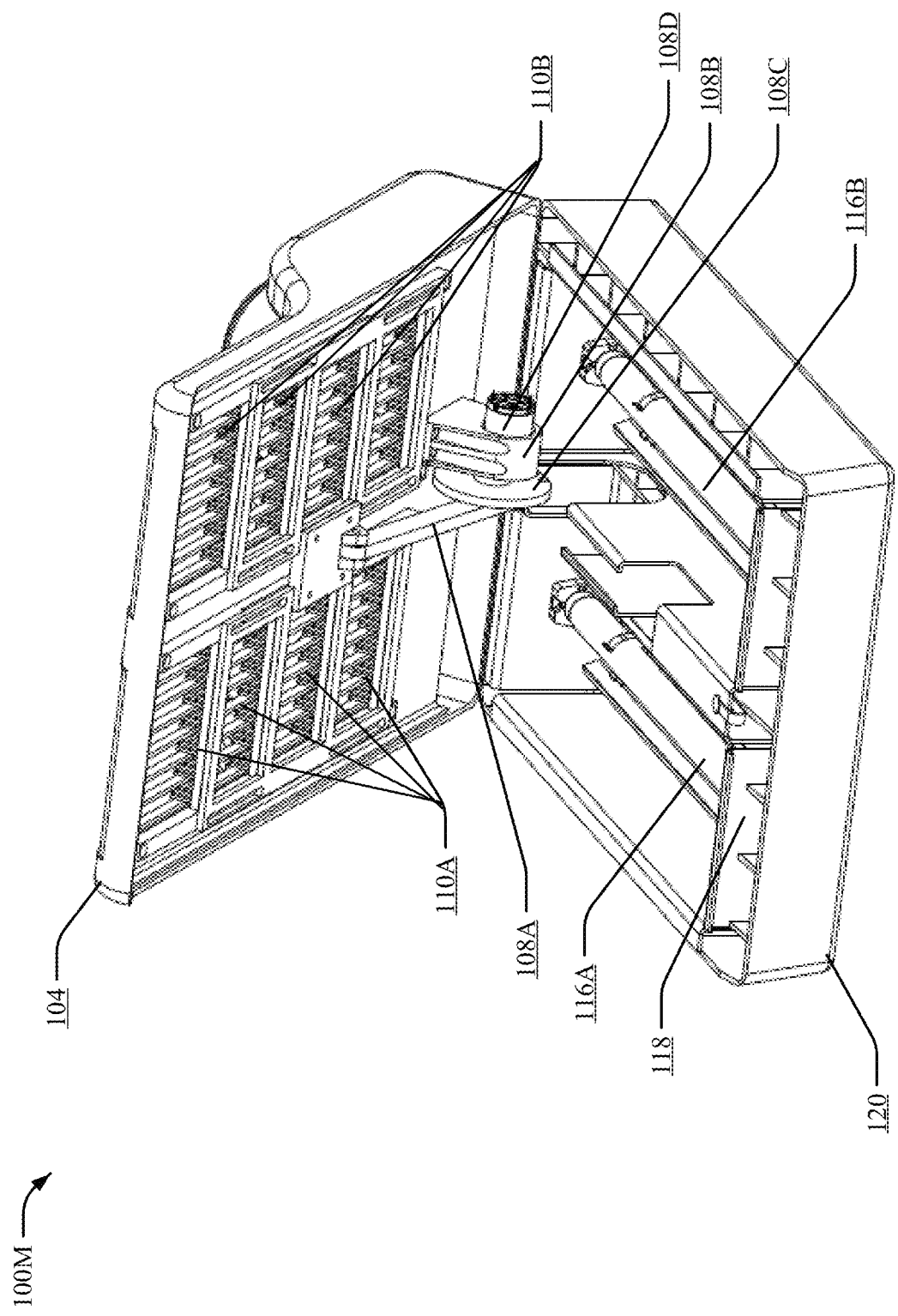
FIG. 1M illustrates another partial side profile view of an example non-limiting system for disinfecting a contaminated item in a partially open position in accordance with one or more implementation described herein.

Turning now to FIG. 1M, illustrated is another partial side profile view of an example non-limiting system for disinfecting a contaminated item in a partially open position in accordance with one or more implementation described herein. Repetitive description of like elements employed in other embodiments described herein is omitted for sake of brevity. In an aspect, system 100M is a different perspective view of system 100A-L. In an aspect, system 100M illustrates top covering element 102, connecting rod 108A, motor mount 108B, can lever element 108C, gear motor 108D, first brush strips 110A, second brush strips 110B, first light assembly 116A, second light assembly 116B, lower frame 118, and bottom covering 120. In an aspect, the components and elements housed within bottom covering 120 are more clearly viewable from the system 100L perspective view.

Figure 1N:
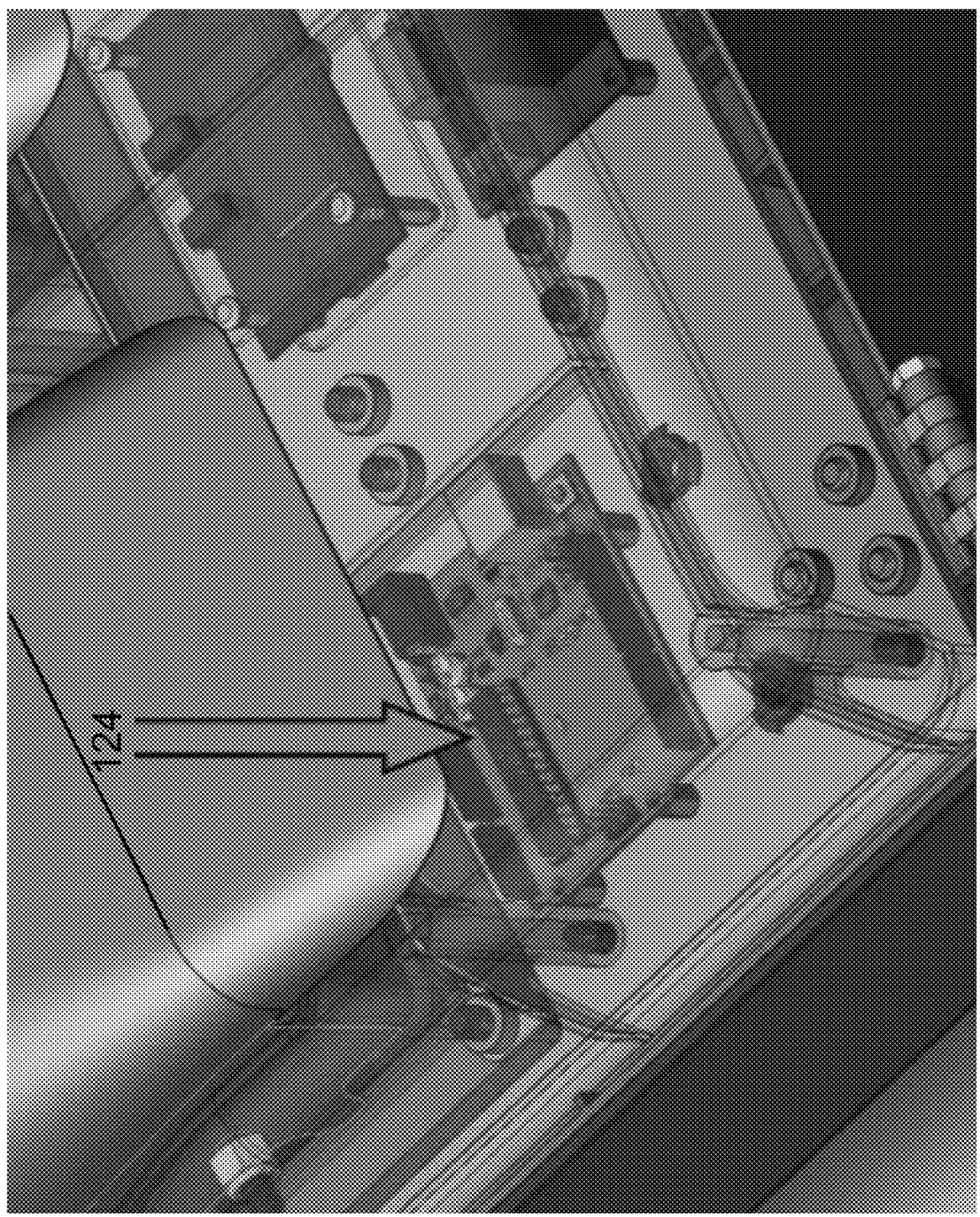
FIG. 1N illustrates a top down view of an example non-limiting microcontroller component of a system for disinfecting a contaminated item in accordance with one or more implementation described herein.

Turning now to FIG. 1N, illustrated is a top down view of an example non-limiting microcontroller component of a system for disinfecting a contaminated item in accordance with one or more implementation described herein. Repetitive description of like elements employed in other embodiments described herein is omitted for sake of brevity. In an aspect, system 100N is a different perspective view of system 100A-M. In an aspect, system 100N illustrates microcontroller 124 capable of executing instructions that perform tasks by system 100N components. For instance, microcontroller 124 can execute instructions that determine a duration that the brush strips perform the brushing operations, the duration an ultraviolet light is emitted by light assemblies, or the motor of the reciprocating device runs. As such, microcontroller 124 can convert instructions into signal for transmission to system 100N components through a series of pins. In an aspect, microcontroller 124 can comprise at least one processor and one or more memory.

Figure 1P:
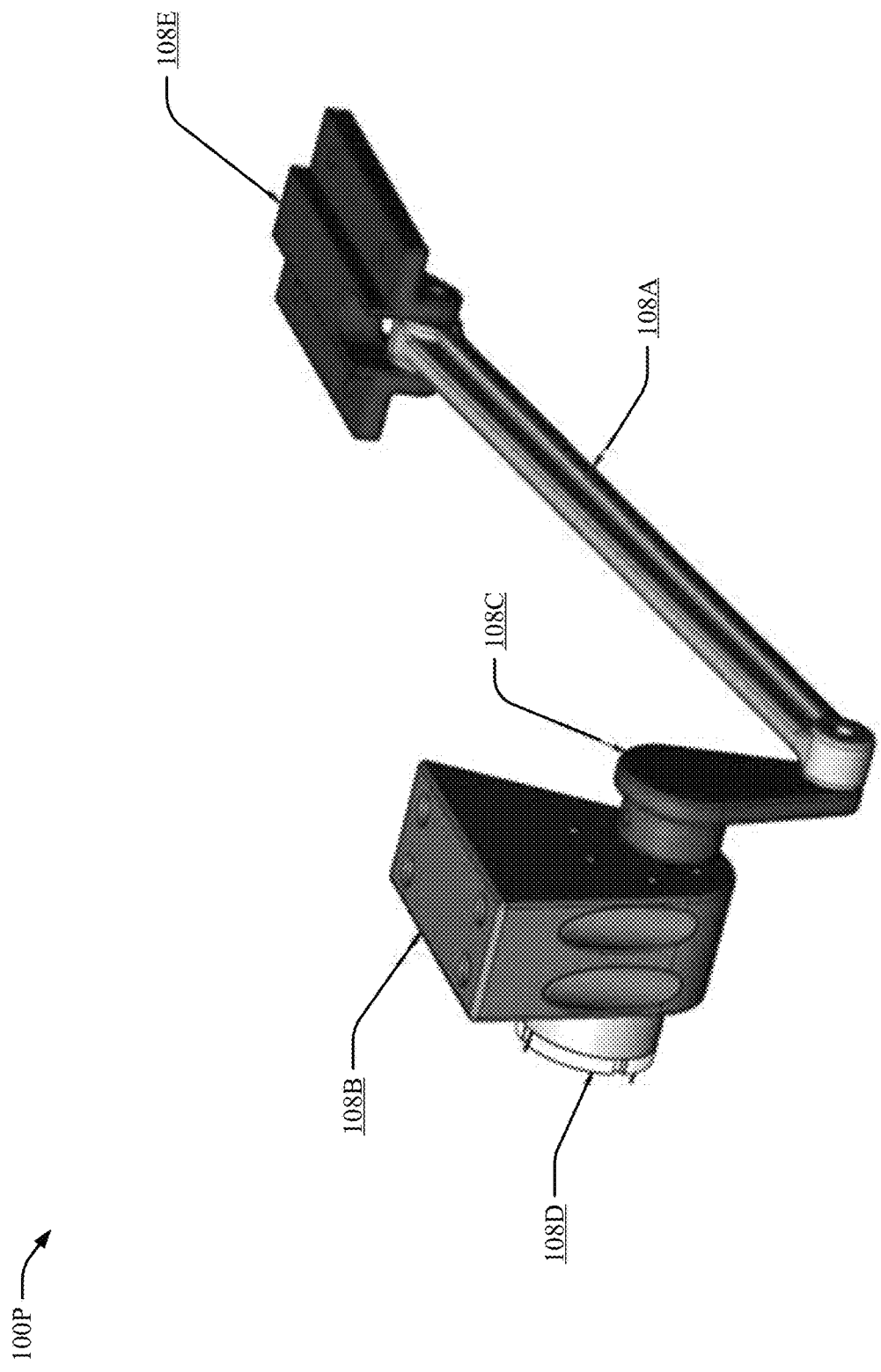
FIG. 1P illustrates an example non-limiting view of a reciprocating drive element of a system for disinfecting a contaminated item in accordance with one or more implementation described herein.

Turning now to FIG. 1P, illustrated is an example non-limiting view of a reciprocating drive element of a system for disinfecting a contaminated item in accordance with one or more implementation described herein. Repetitive description of like elements employed in other embodiments described herein is omitted for sake of brevity. In an aspect, system 100P is a different perspective view of system 100A-N. In an aspect, illustrated is reciperocating drive 108. In an aspect, reciprocating drive 108 can include connecting rod 108A, motor mount 108B, cam lever element 108C, gear motor 108D, and brush drive mount 108E.

In an aspect, as gear motor 108D rotates, the cam lever element 108C also rotates thus pushing connecting rod 108A forward and backwards in a back and forth motion. Furthermore, in an aspect, brush drive mount 108E also moves forward and backward and such brush drive mount 108E can be configured to connect with first brush frame 112A and second brush frame 112B. As such, first brush frame 112A and second brush frame 112B can move forawrd and backward as well. Furthermore, the brush drive mount 108E can be connected to the central region of the brush frame as well as second brush guide 114B and third brush guide 114C which can result in a brushing motion of the set of brushes in a forward and back manner thus sweeping debris from the lower surface of a footwear item.

Turning now to FIG. 1Q, illustrated is an example non-limiting view of an underside of a top plate element of a system for disinfecting a contaminated item in accordance with one or more implementation described herein. Repetitive description of like elements employed in other embodiments described herein is omitted for sake of brevity. In an aspect, system 100Q is a different perspective view of system 100A-P. In an aspect, system 100Q illustrates a lower view of top plate element 106. Illustrated are first grating element 104A, second grating element 104B, top plate element 106, reciprocating drive 108 (comprising connecting rod 108A, motor mount 108B, cam lever element 108C, gear motor 108D, and brush drive mount 108E), first brush frame 112A, second brush frame 112B, first brush guide 114A, second brush guide 114B, third brush guide 114C, and fourth brush guide 114D. Also, illustrated are two hinges which allow the top plate element 106 to open and close allowing access to component parts of system 100Q. For instance, by opening top plate element 106, elements affixed to the bottom surface of top plate element 106 can be accessed as well as elements in lower frame 118 and/or bottom covering element 120.

While the methods described within this disclosure are illustrated in and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases. Reference may be made to the figures described avoec for ease of description. However, the methods are not limited to any particular emodiment or example provided within this disclosure and can be applied to any of the systems disclosed herein.

Figure 1R:
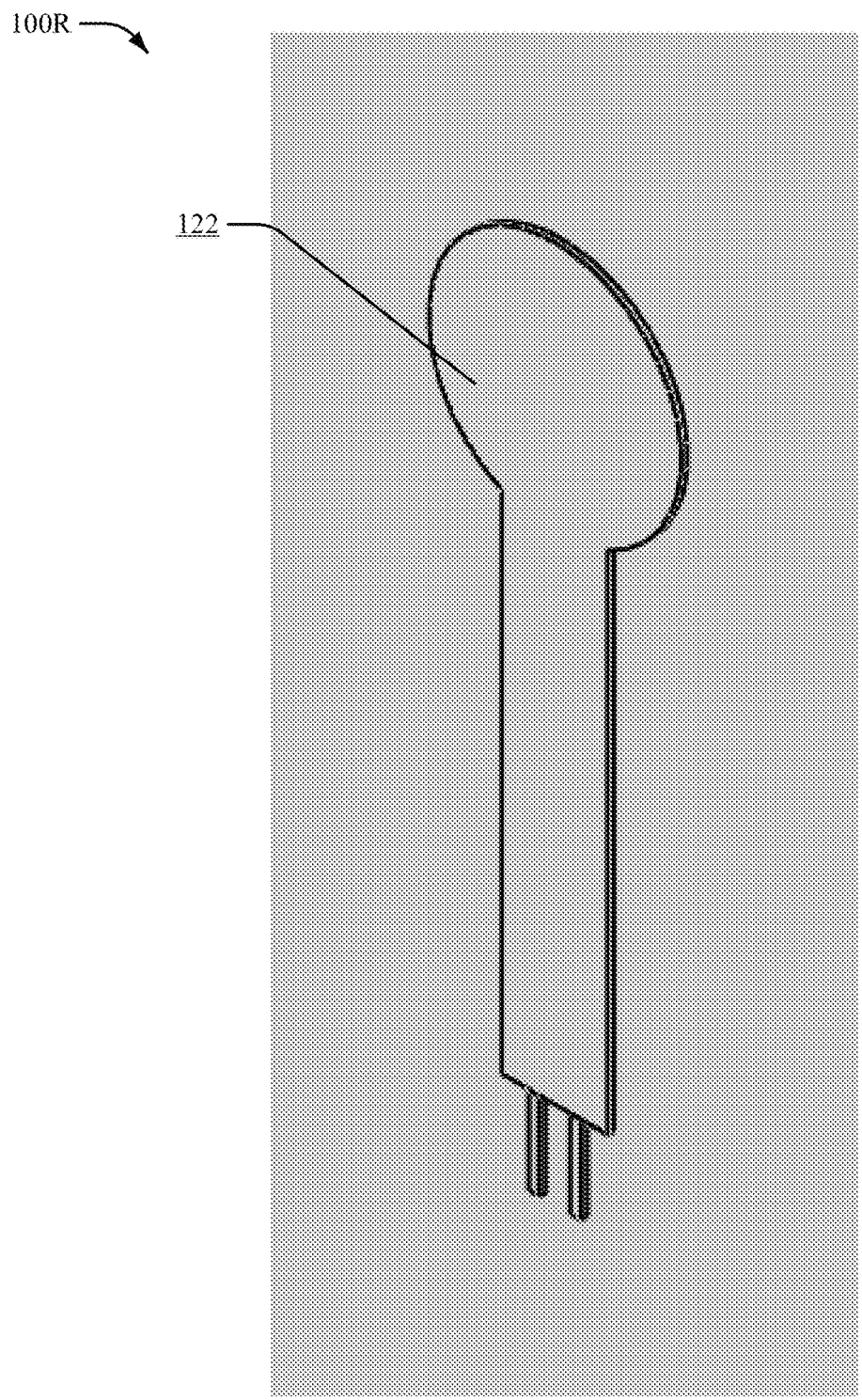
FIG. 1R illustrates an example non-limiting weight sensor element of a system for disinfecting a contaminated item in accordance with one or more implementation described herein.

FIG. 1R illustrates an example non-limiting weight sensor element 122 of a system 100R for disinfecting a contaminated item in accordance with one or more implementation described herein. Repetitive description of like elements employed in other embodiments described herein is omitted for sake of brevity. In an aspect, weight sensor 122 can be embedded within any of systems 100A-Q in order to facilitate detection of a force applied to the systems 100A-Q. Upon detection of a force applied to systems 100A-Q, the system can be activated or remain deactivated. For instance, if weight sensor 122 detects a force applied to systems 100A-Q that is greater than a threshold force (e.g., indicating an adult has stepped onto the disinfecting system) then system 100A-Q can be activated to perform the disinfecting and cleaning operations. In another instance, if weight sensor 122 detects a force applied to systems 100A-Q that is below a threshold force, then systems 100A-Q can remain deactivated in order to prevent the system from activation upon a child using such system.

Figure 1S:
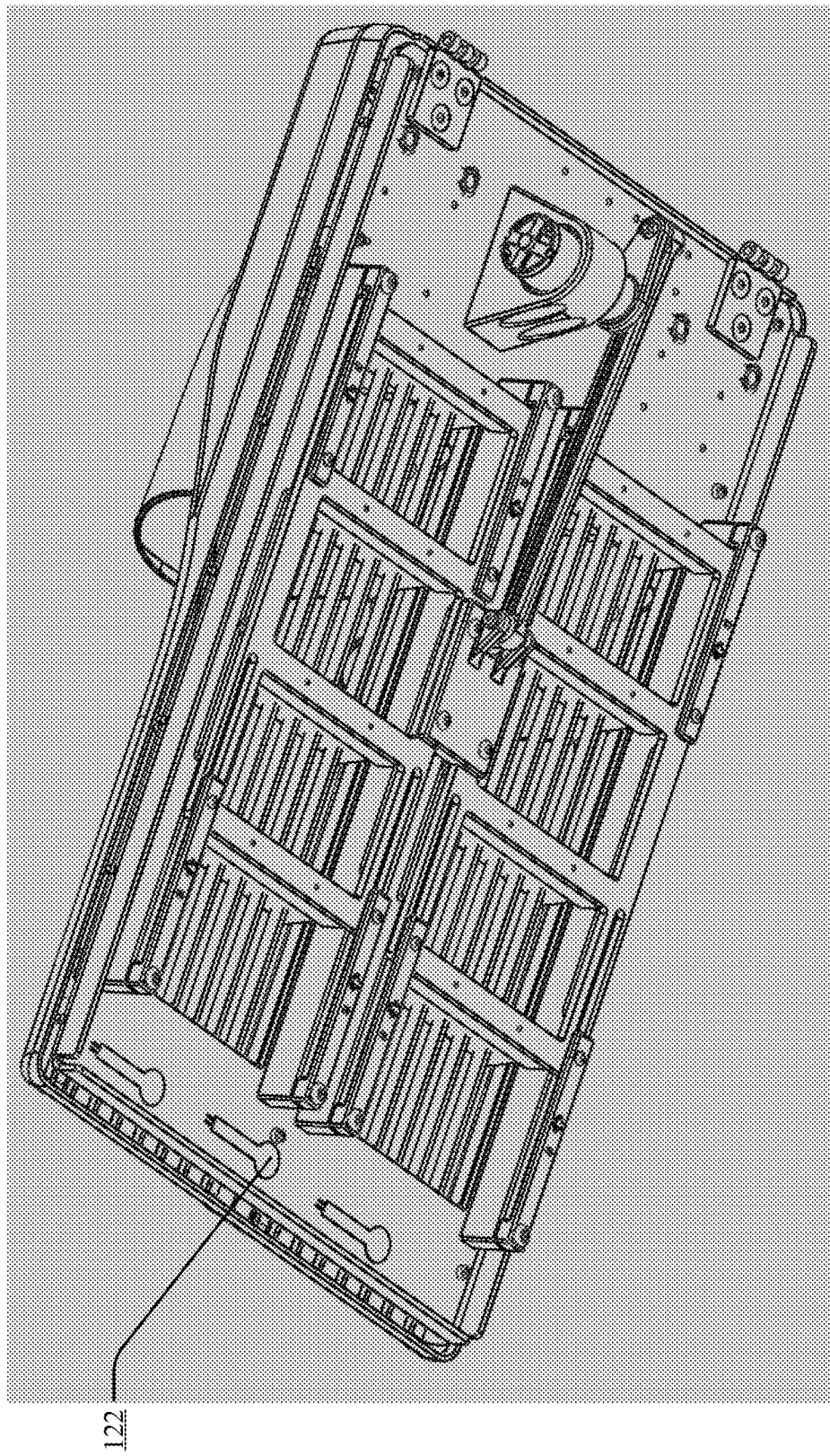
FIG. 1S illustrates an example non-limiting weight sensor element located on an underside of a top plate element of a system for disinfecting a contaminated item in accordance with one or more implementation described herein.

FIG. 1S illustrates an example non-limiting weight sensor element located on an underside of a top plate element of a system for disinfecting a contaminated item in accordance with one or more implementation described herein. Repetitive description of like elements employed in other embodiments described herein is omitted for sake of brevity. In an aspect, system 100S illustrates an embodiment with weight sensors 122 located on the underside of top plate element 106. As such, each weight sensor 122 can be positioned at any of several locations on systems 100A-S in order to detect a force applied to top plate element 106 (e.g., from a user standing upon grating elements).

Figure 1T:
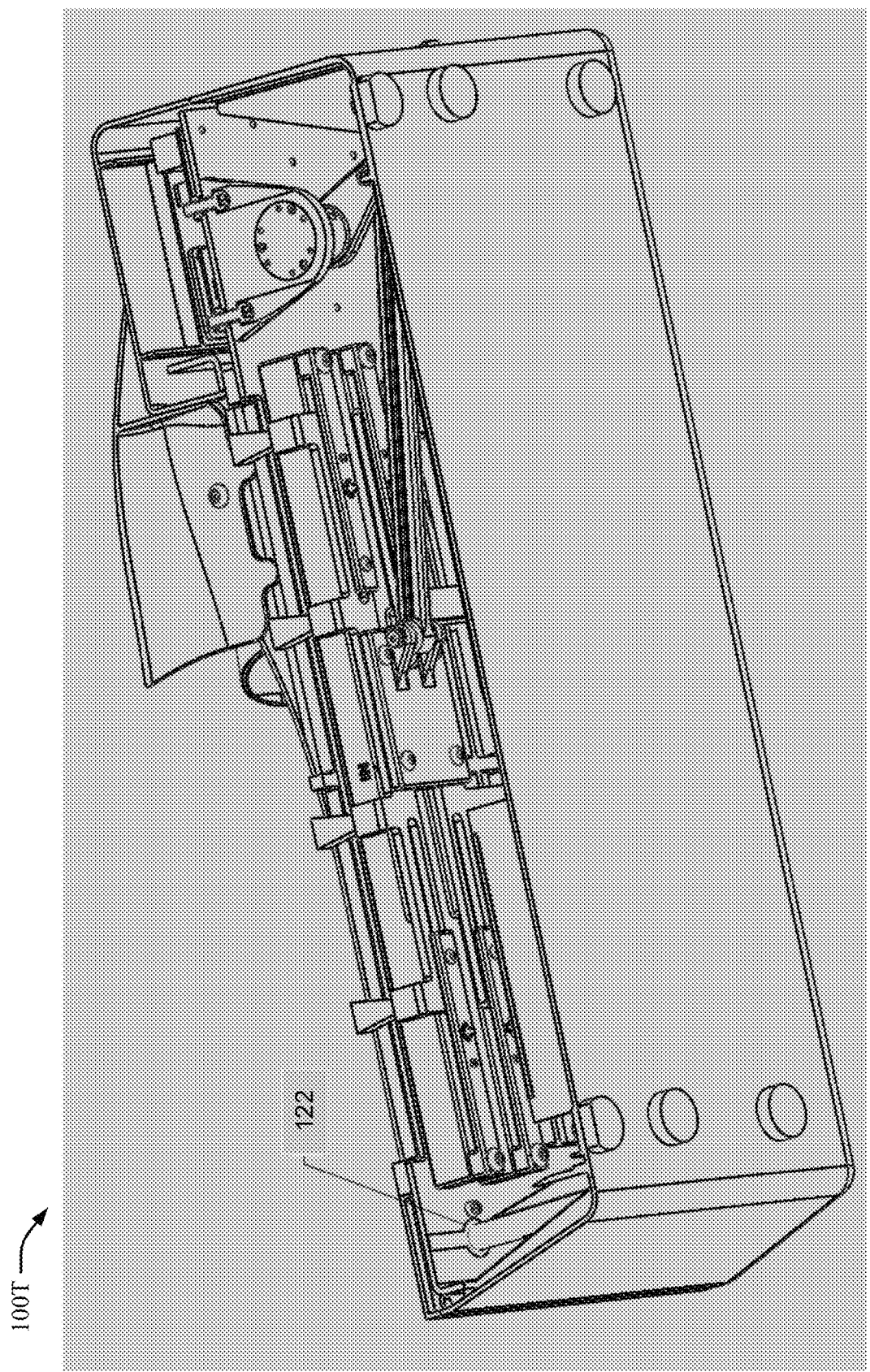
FIG. 1T illustrates an example non-limiting weight sensor element located on an underside of a top plate element of a system for disinfecting a contaminated item in accordance with one or more implementation described herein.

FIG. 1T illustrates an example non-limiting weight sensor element located on an underside of a top plate element of a system for disinfecting a contaminated item in accordance with one or more implementation described herein. In an aspect, system 100T illustrates an embodiment with weight sensors 122 located on the underside of top plate element 106. Furthermore, a ledge of lower frame 118 and/or bottom covering element 120 can make contact with the weight sensor upon a force being applied to top plate element 106 in order to detect an applied force to systems 100A-T. In a non-limiting embodiment, the weight sensors can detect the force between top plate element 106 and lower frame 118 and.or bottom covering element 120 as the applied force.

Figure 2:
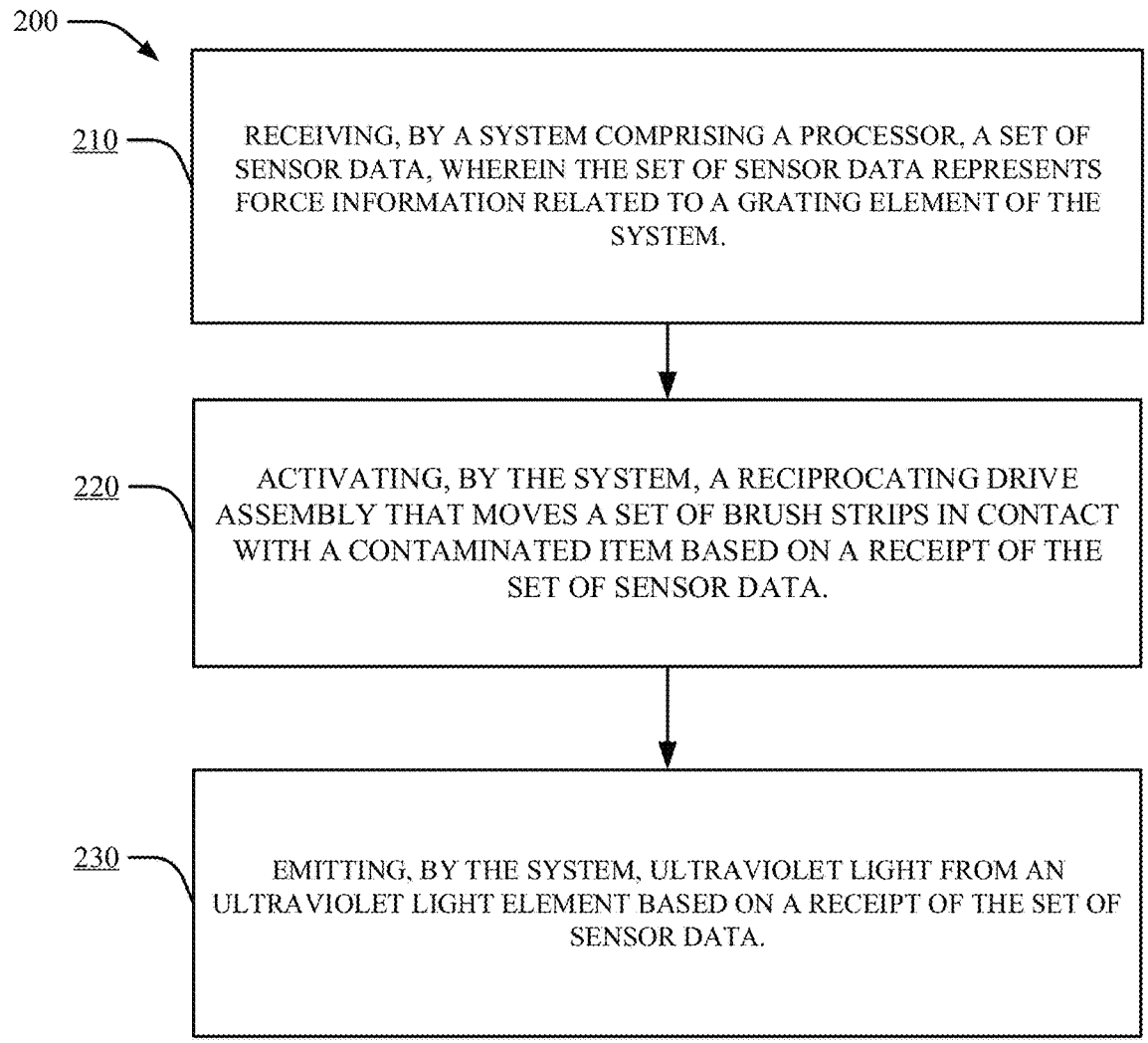
FIG. 2 illustrates an example methodology for disinfecting a contaminated item using an apparatus in accordance with one or more implementation described herein.

FIG. 2, illustrates an example methodology 200 for disinfecting a contaminated item using an apparatus in accordance with one or more implementation described herein. At 210, a set of sensor data can be received by a system comprising a processor, wherein the set of sensor data represents force information related to a grating element of the system. At 220, a reciprocating drive assembly of the system can be activated to move a set of brush strips in contact with a contaminated item based on a receipt of the set of sensor data. At 230, an ultraviolet light of the system can be emitted from an ultraviolet light element based on a receipt of the set of sensor data.

Figure 3:
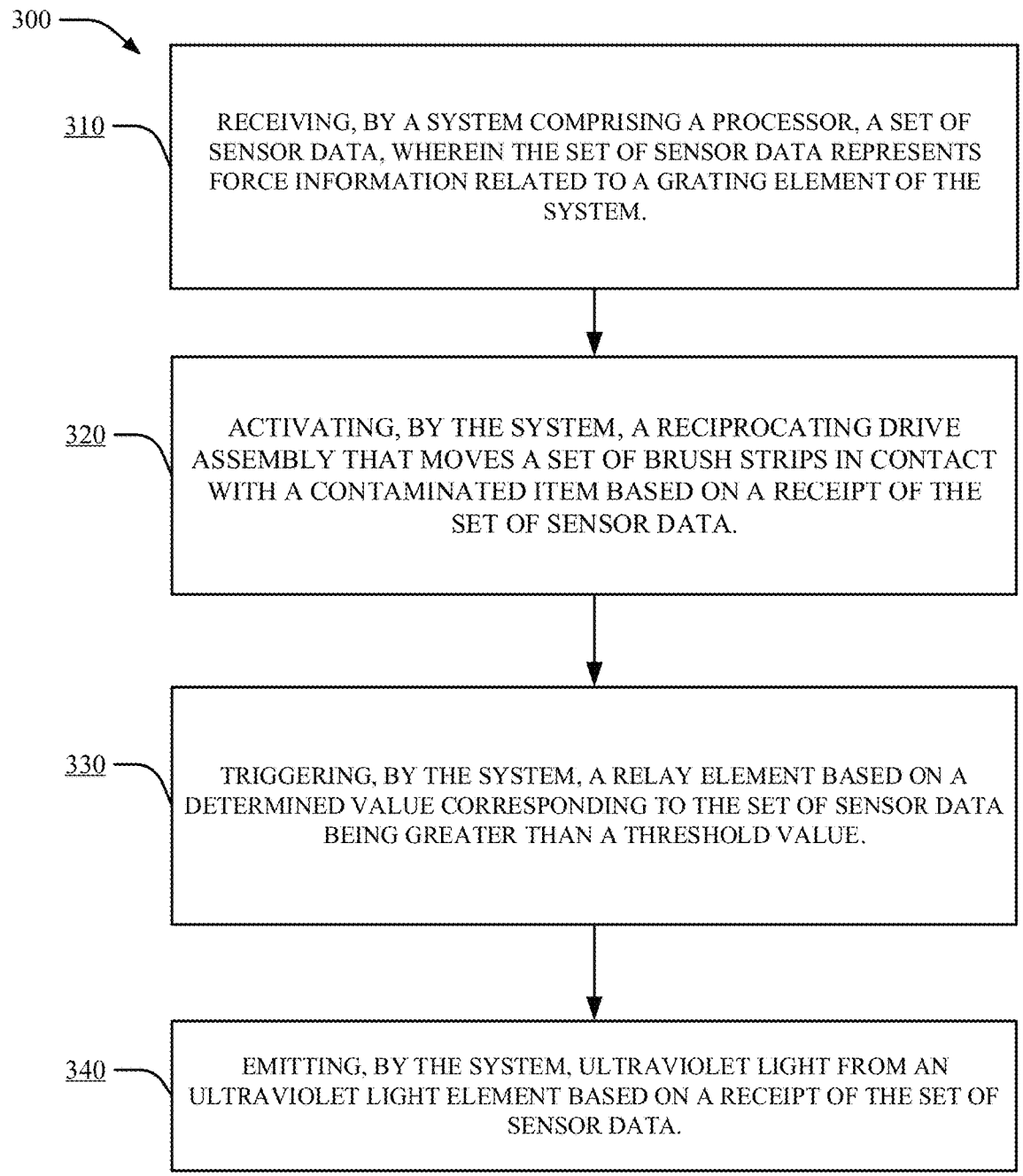
FIG. 3 illustrates an example methodology for disinfecting a contaminated item using an apparatus in accordance with one or more implementation described herein.

FIG. 3, illustrates an example methodology 300 for disinfecting a contaminated item using an apparatus in accordance with one or more implementation described herein. At 310, a set of sensor data can be received by a system comprising a processor, wherein the set of sensor data represents force information related to a grating element of the system. At 320, a reciprocating drive assembly of the system can be activated to move a set of brush strips in contact with a contaminated item based on a receipt of the set of sensor data. At 330, a relay element of the system is triggered based on a determined value corresponding to the set of sensor data being greater than a threshold value. At 340, an ultraviolet light of the system can be emitted from an ultraviolet light element based on a receipt of the set of sensor data.

Figure 4:
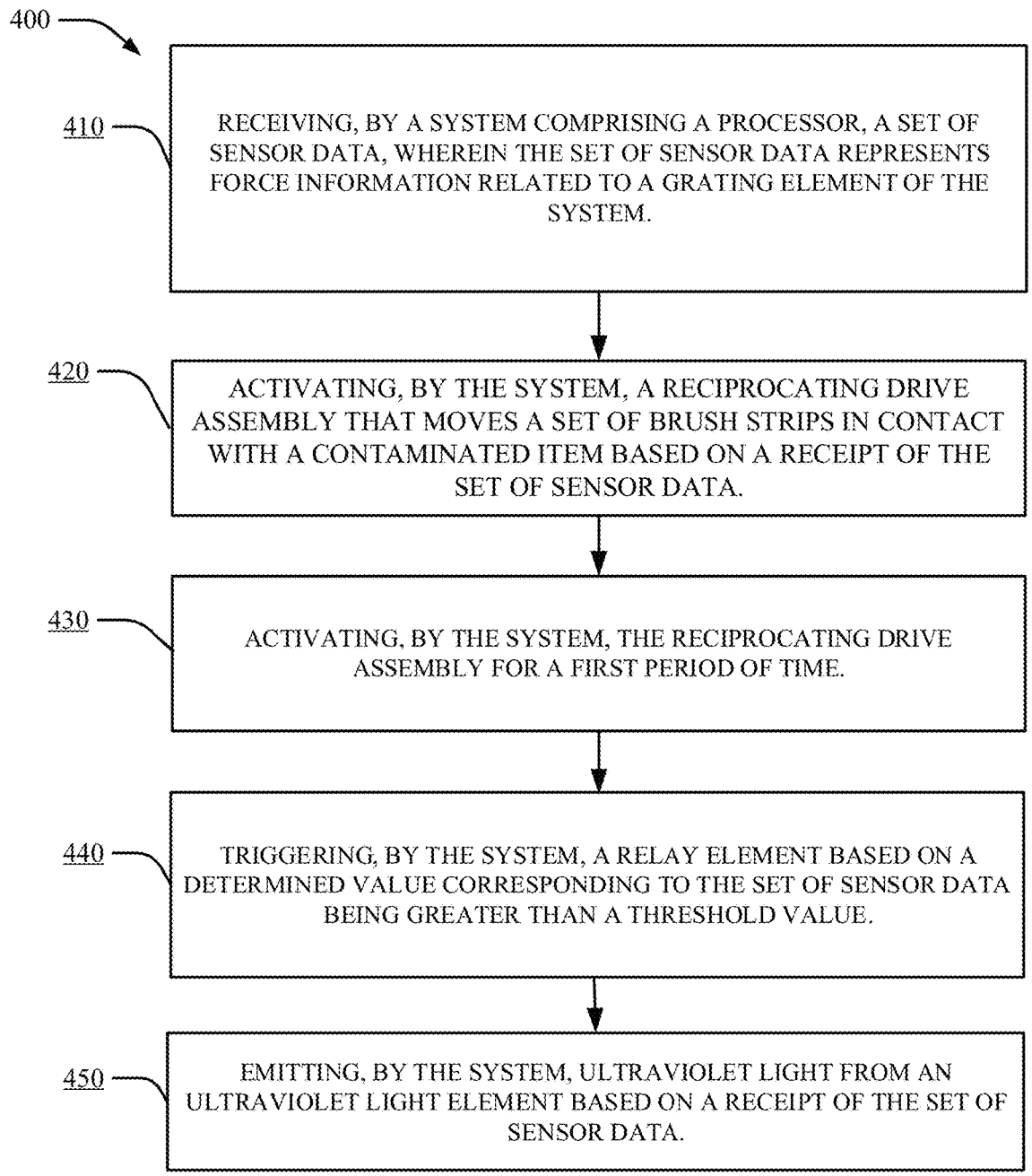
FIG. 4 illustrates an example methodology for disinfecting a contaminated item using an apparatus in accordance with one or more implementation described herein.

FIG. 4, illustrates an example methodology 400 for disinfecting a contaminated item using an apparatus in accordance with one or more implementation described herein. At 410, a set of sensor data can be received by a system comprising a processor, wherein the set of sensor data represents force information related to a grating element of the system. At 420, a reciprocating drive assembly of the system can be activated to move a set of brush strips in contact with a contaminated item based on a receipt of the set of sensor data. At 430, the reciprocating drive assembly can be activated by the sytem for a first determined period of time. At 440, a relay element of the system is triggered based on a determined value corresponding to the set of sensor data being greater than a threshold value. At 450, an ultraviolet light of the system can be emitted from an ultraviolet light element based on a receipt of the set of sensor data.

Figure 5:
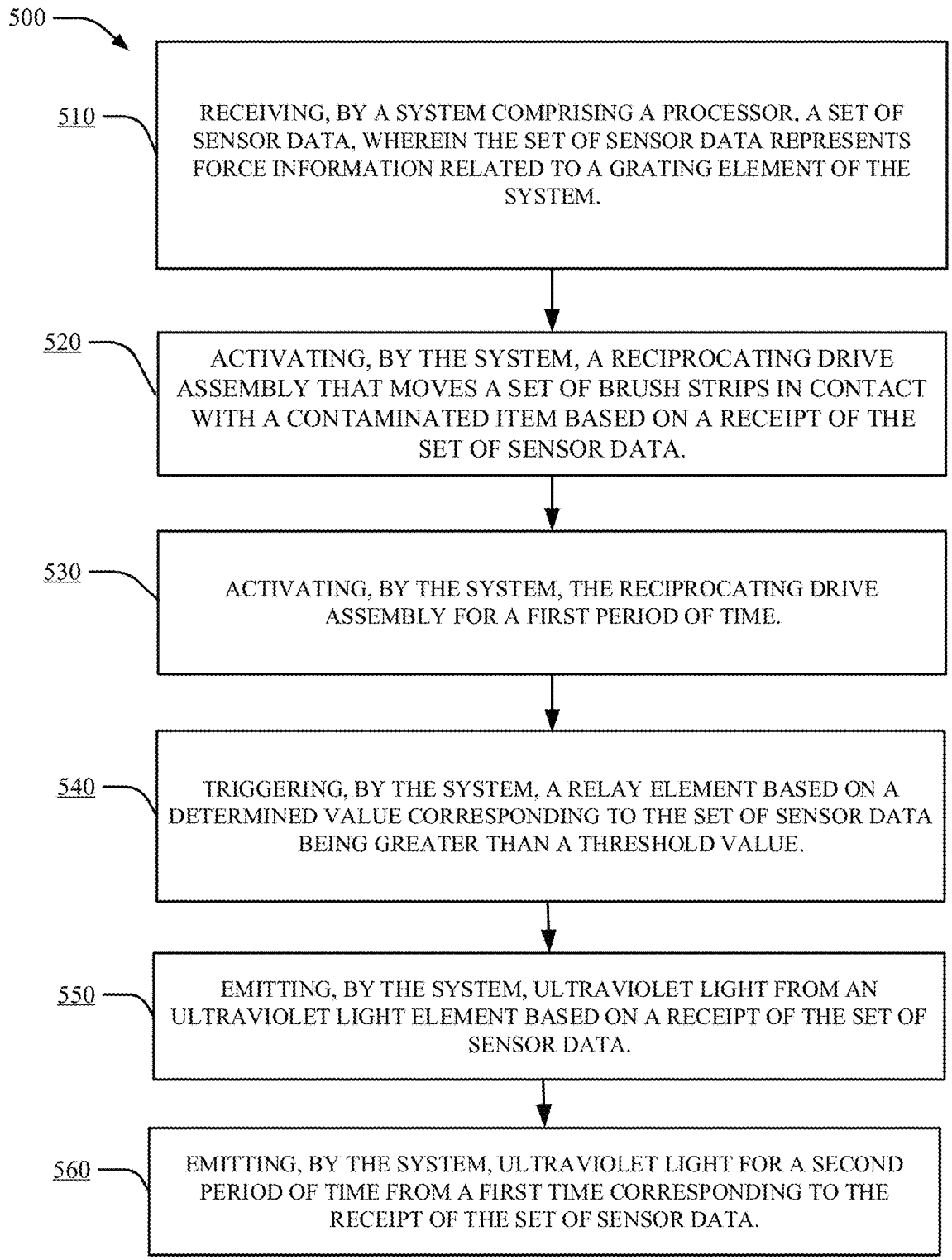
FIG. 5 illustrates an example methodology for disinfecting a contaminated item using an apparatus in accordance with one or more implementation described herein.

FIG. 5, illustrates an example methodology 500 for disinfecting a contaminated item using an apparatus in accordance with one or more implementation described herein. At 510, a set of sensor data can be received by a system comprising a processor, wherein the set of sensor data represents force information related to a grating element of the system. At 520, a reciprocating drive assembly of the system can be activated to move a set of brush strips in contact with a contaminated item based on a receipt of the set of sensor data. At 530, the reciprocating drive assembly can be activated by the sytem for a first determined period of time. At 540, a relay element of the system is triggered based on a determined value corresponding to the set of sensor data being greater than a threshold value. At 550, an ultraviolet light of the system can be emitted from an ultraviolet light element based on a receipt of the set of sensor data. At 560, the ultraviolet light of the system can be emitted for a second determined period of time from a first time corresponding to the receipt of the set of sensor data.

Figure 6:
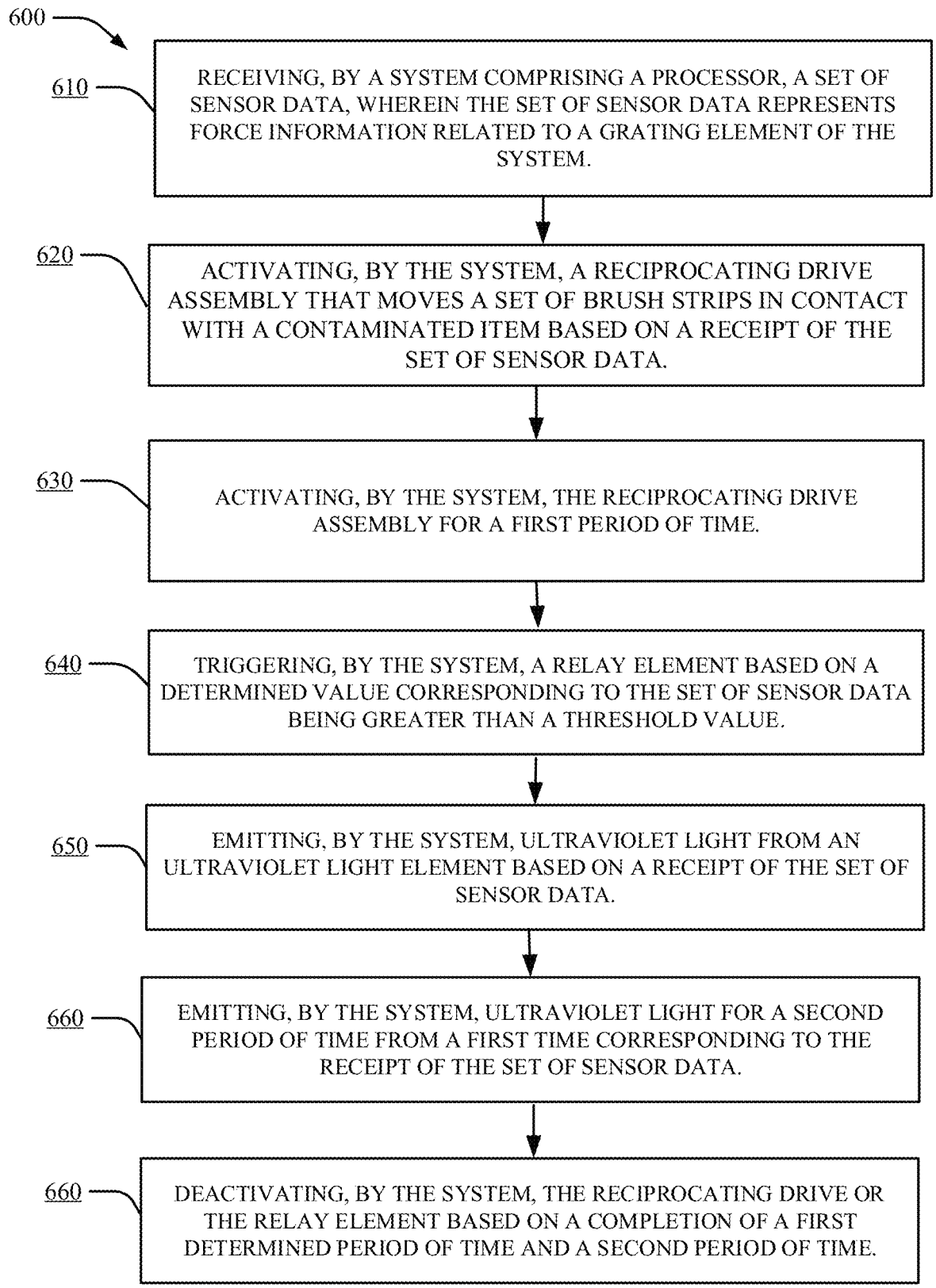
FIG. 6 illustrates an example methodology for disinfecting a contaminated item using an apparatus in accordance with one or more implementation described herein.

FIG. 6, illustrates an example methodology 600 for disinfecting a contaminated item using an apparatus in accordance with one or more implementation described herein. At 610, a set of sensor data can be received by a system comprising a processor, wherein the set of sensor data represents force information related to a grating element of the system. At 620, a reciprocating drive assembly of the system can be activated to move a set of brush strips in contact with a contaminated item based on a receipt of the set of sensor data. At 630, the reciprocating drive assembly can be activated by the sytem for a first determined period of time. At 640, a relay element of the system is triggered based on a determined value corresponding to the set of sensor data being greater than a threshold value. At 650, an ultraviolet light of the system can be emitted from an ultraviolet light element based on a receipt of the set of sensor data. At 660, the ultraviolet light of the system can be emitted for a second determined period of time from a first time corresponding to the receipt of the set of sensor data. At 670, the reciprcaoting drive or the relay element of the system can be deactivated based on a completion of a first determined period of time and a second period of time.

Figure 7:
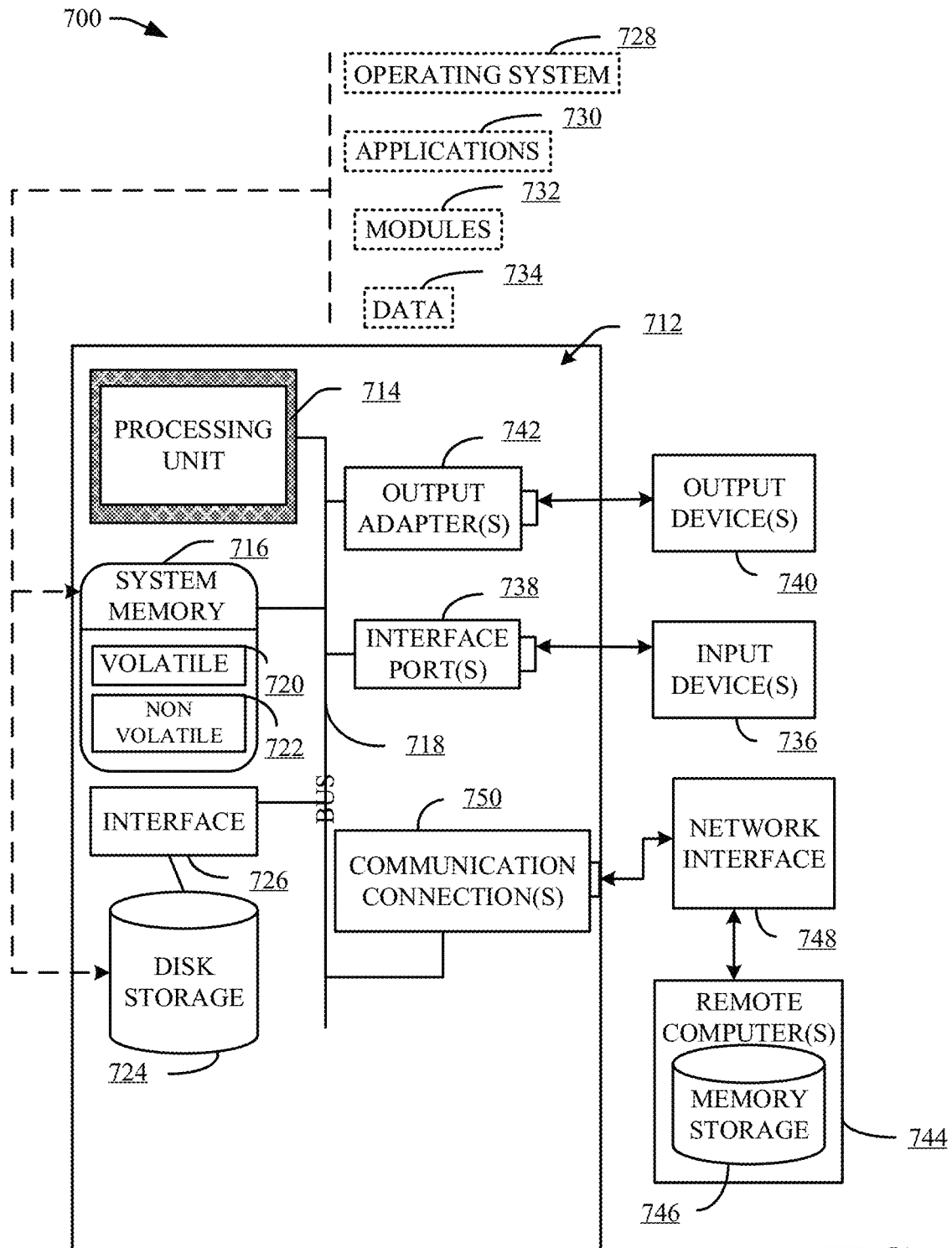
FIG. 7 illustrates an example methodology for disinfecting a contaminated item using an apparatus in accordance with one or more implementation described herein.

In order to provide a context for the various aspects of the disclosed subject matter, FIG. 7 as well as the following discussion is intended to provide a general description of a suitable environment in which the various aspects of the disclosed subject matter can be implemented. FIG. 7 illustrates a block diagram of an example, non-limiting operating environment in which one or more embodiments described herein can be facilitated. With reference to FIG. 7, a suitable operating environment 700 for implementing various aspects of this disclosure can also include a computer 712. The computer 712 can also include a processing unit 714, a system memory 716, and a system bus 718. The system bus 718 couples system components including, but not limited to, the system memory 716 to the processing unit 714. The processing unit 714 can be any of various available processors. Dual microprocessors and other multiprocessor architectures also can be employed as the processing unit 714. The system bus 718 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 716 can also include volatile memory 720 and nonvolatile memory 722. The basic input/output system (BIOS), containing the basic routines to transfer information between elements within the computer 712, such as during start-up, is stored in nonvolatile memory 722. By way of illustration, and not limitation, nonvolatile memory 722 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 720 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DR-RAM), direct Rambus dynamic RAM (DRDRAM), and Rambus dynamic RAM.

Computer 712 can also include removable/non-removable, volatile/non-volatile computer storage media. FIG. 7 illustrates, for example, a disk storage 724. Disk storage 724 can also include, but is not limited to, devices like a magnetic disk drive, floppy disk drive, tape drive, Jaz drive, Zip drive, LS-100 drive, flash memory card, or memory stick. The disk storage 724 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 724 to the system bus 718, a removable or non-removable interface is typically used, such as interface 726. FIG. 7 also depicts software that acts as an intermediary between users and the basic computer resources described in the suitable operating environment 700. Such software can also include, for example, an operating system 728. Operating system 728, which can be stored on disk storage 724, acts to control and allocate resources of the computer 712.

System applications 730 take advantage of the management of resources by operating system 728 through program modules 732 and program data 734, e.g., stored either in system memory 716 or on disk storage 724. It is to be appreciated that this disclosure can be implemented with various operating systems or combinations of operating systems. A user enters commands or information into the computer 712 through input device(s) 736. Input devices 736 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 714 through the system bus 718 via interface port(s) 738. Interface port(s) 738 include, for example, a serial port, a parallel port, a game port, and a universal serial bus (USB). Output device(s) 740 use some of the same type of ports as input device(s) 736. Thus, for example, a USB port can be used to provide input to computer 712, and to output information from computer 712 to an output device 740. Output adapter 1242 is provided to illustrate that there are some output device 740 like monitors, speakers, and printers, among other such output device 740, which require special adapters. The output adapters 742 include, by way of illustration and not limitation, video and sound cards that provide a means of connection between the output device 740 and the system bus 718. It should be noted that other devices and/or systems of devices provide both input and output capabilities such as remote computer(s) 744.

Computer 712 can operate in a networked environment using logical connections to one or more remote computers, such as remote computer(s) 744. The remote computer(s) 744 can be a computer, a server, a router, a network PC, a workstation, a microprocessor based appliance, a peer device or other common network node and the like, and typically can also include many or all of the elements described relative to computer 712. For purposes of brevity, only a memory storage device 746 is illustrated with remote computer(s) 744. Remote computer(s) 744 is logically connected to computer 712 through a network interface 748 and then physically connected via communication connection 750. Network interface 748 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 750 refers to the hardware/software employed to connect the network interface 748 to the system bus 718. While communication connection 750 is shown for illustrative clarity inside computer 712, it can also be external to computer 712. The hardware/software for connection to the network interface 748 can also include, for exemplary purposes only, internal and external technologies such as, modems including regular telephone grade modems, cable modems and DSL modems, ISDN adapters, and Ethernet cards.

Figure 8:
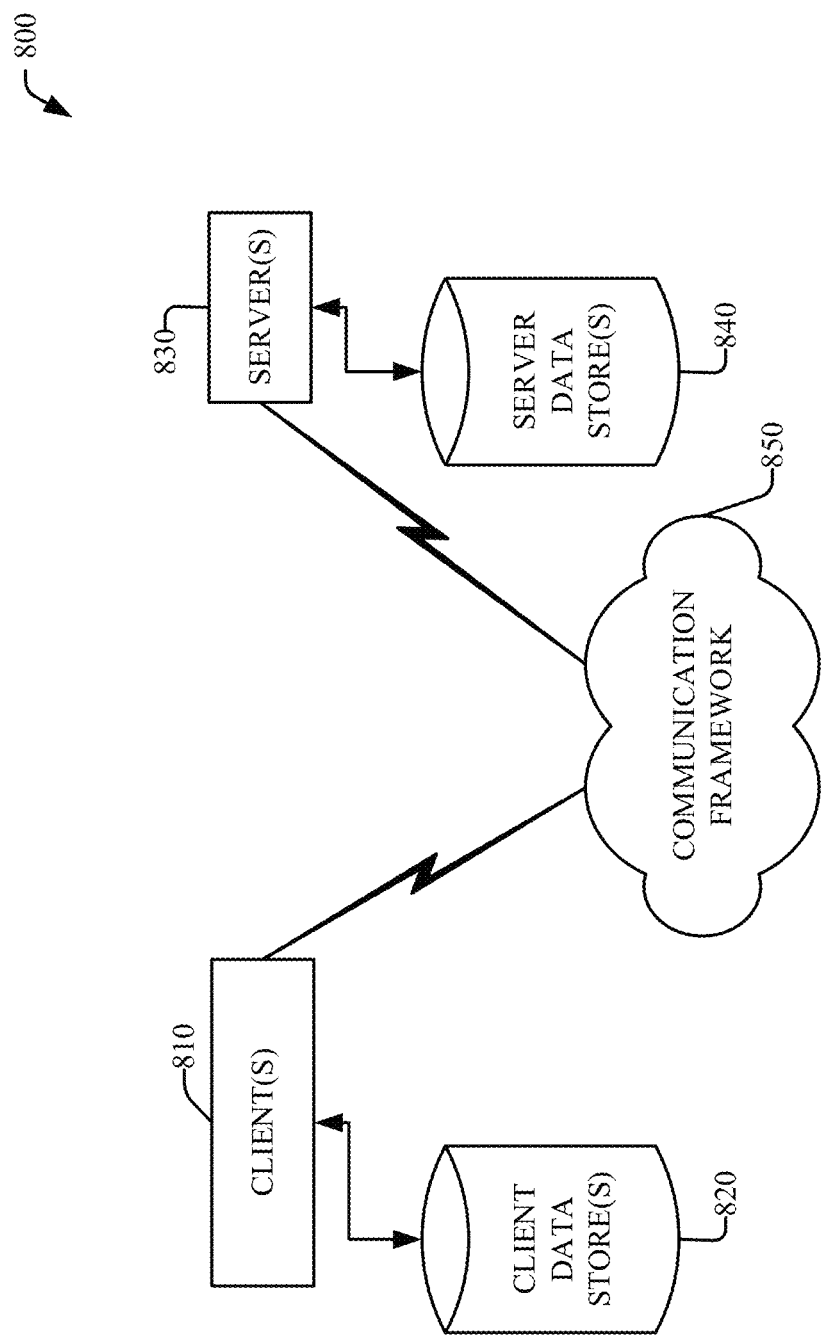
FIG. 8 is a schematic block diagram illustrating a suitable operating environment in accordance with various aspects and embodiments.

Referring now to FIG. 8, there is illustrated a schematic block diagram of a computing environment 800 in accordance with this disclosure. The system 800 includes one or more client(s) 802 (e.g., laptops, smart phones, PDAs, media players, computers, portable electronic devices, tablets, and the like). The client(s) 802 can be hardware and/or software (e.g., threads, processes, computing devices). The system 800 also includes one or more server(s) 804. The server(s) 804 can also be hardware or hardware in combination with software (e.g., threads, processes, computing devices). The servers 804 can house threads to perform transformations by employing aspects of this disclosure, for example. One possible communication between a client 802 and a server 804 can be in the form of a data packet transmitted between two or more computer processes wherein the data packet may include video data. The data packet can include a metadata, e.g., associated contextual information, for example. The system 800 includes a communication framework 806 (e.g., a global communication network such as the Internet, or mobile network(s)) that can be employed to facilitate communications between the client(s) 802 and the server(s) 804.

Communications can be facilitated via a wired (including optical fiber) and/or wireless technology. The client(s) 802 include or are operatively connected to one or more client data store(s) 808 that can be employed to store information local to the client(s) 802 (e.g., associated contextual information). Similarly, the server(s) 804 are operatively include or are operatively connected to one or more server data store(s) 810 that can be employed to store information local to the servers 804. In one embodiment, a client 802 can transfer an encoded file, in accordance with the disclosed subject matter, to server 804. Server 804 can store the file, decode the file, or transmit the file to another client 802. It is to be appreciated, that a client 802 can also transfer uncompressed file to a server 804 and server 804 can compress the file in accordance with the disclosed subject matter. Likewise, server 804 can encode video information and transmit the information via communication framework 806 to one or more clients 802.

The present disclosure may be a system, a method, an apparatus and/or a computer program product at any possible technical detail level of integration. The computer program product can include a computer readable storage medium (or media) having computer readable program instructions thereon for causing a processor to carry out aspects of the present disclosure. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible.

Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    receiving, by a system comprising a processor, a set of sensor data, wherein the set of sensor data represents force information related to a grating element of the system;
    activating, by the system, a reciprocation drive assembly of the system that moves a set of brush strips in contact with a contaminated item based on a receipt of the set of sensor data; and
    emitting, by the system, ultraviolet light from an ultraviolet light element based on a receipt of the set of sensor data.

2. The method of claim 1, further comprising triggering, by the system, a relay element based on a determined value corresponding to the set of sensor data being greater than a threshold value.

3. The method of claim 2, further comprising deactivating, by the system, the reciprocation drive assembly or the relay element based on a termination of a first period of time and a second period of time.

4. The method of claim 3, further comprising resetting, by the system, a force detection sensor based on a deactivation of the reciprocation drive or the relay element.

5. The method of claim 1, further comprising activating, by the system, the reciprocation drive assembly for a first period of time.

6. The method of claim 1, further comprising emitting, by the system, ultraviolet light for a second period of time commencing at a first start time based on a receipt of the set of sensor data.

7. A method comprising:
    emitting ultraviolet light, by an ultraviolet light element of a device, toward a top covering element configured to receive one or more contaminated item, wherein the ultraviolet light element is located within a lower frame element;
    receiving, by a grating element of the device, one or more contaminated item; wherein the grating element is a ceiling enclosure portion of the lower frame element; and
    brushing, by a set of brush strips of the device, an underside of the one or more contaminated items.

8. The method of claim 7, further comprising blocking at least a portion of the emitted ultraviolet light emanating from the ultraviolet light element using an awning portion of a top cover element of the device.

9. The method of claim 7, further comprising detecting, by a sensor element of the device, an amount of force applied to the grating element.

10. The method of claim 7, further comprising activating, by an activation element of the device, at least one of the set of brush strips or the ultraviolet light element based on a detected force value corresponding to a detected amount of force being greater than a threshold force value.

\* \* \* \* \*